US006018713A

United States Patent [19]
Coli et al.

[11] Patent Number: 6,018,713
[45] Date of Patent: Jan. 25, 2000

[54] INTEGRATED SYSTEM AND METHOD FOR ORDERING AND CUMULATIVE RESULTS REPORTING OF MEDICAL TESTS

[76] Inventors: Robert D. Coli, 300 Tollgate Rd., Warwick, R.I. 02886; Lily Goykhman; Dmitry Goykhman, both of 132 Main St., Acton, Mass. 01720

[21] Appl. No.: 09/057,560

[22] Filed: Apr. 9, 1998

Related U.S. Application Data

[60] Provisional application No. 60/041,853, Apr. 9, 1997.

[51] Int. Cl.[7] .................................................... G06F 17/60
[52] U.S. Cl. ............................ 705/2; 705/1; 705/3; 705/4
[58] Field of Search ................................... 705/2, 3, 4, 1; 128/920; 702/19; 600/300

[56] References Cited

U.S. PATENT DOCUMENTS

| | | | |
|---|---|---|---|
| 5,065,315 | 11/1991 | Garcia .......................................... | 705/2 |
| 5,301,105 | 4/1994 | Cummings, Jr. .............................. | 705/2 |
| 5,366,896 | 11/1994 | Margrey et al. ........................... | 436/48 |
| 5,722,418 | 3/1998 | Bro ................................................... | 1/1 |
| 5,748,907 | 5/1998 | Crane .......................................... | 705/2 |
| 5,769,074 | 6/1998 | Barnhill et al. .......................... | 128/630 |

OTHER PUBLICATIONS

Eisenberg et al; How Will Changes in Physician Payment by Medecine Influence Laboratory Testing? American Medical Association; Dialogue: File, 442 ; Account No.00015825, Aug. 1987.

Arthur; Evaluation of the Tri–Service Laboratory System. Vol. 1. Overview and Executive Summary; Dialogue, file: 6, Account No. 1101290, Jun. 1993.

Factors affecting the choice of laboratories for clinical trials; Drug Information Journal; Dialogue, file: 73:EMBASE, Account No. 06588804, Mar. 1996.

*Primary Examiner*—Allen R. MacDonald
*Assistant Examiner*—Romain Jeanty
*Attorney, Agent, or Firm*—Evan R. Smith; Greenberg Traurig

[57] ABSTRACT

A network-based system and method for ordering and cumulative results reporting of medical tests includes a computer operated at a physician location (such as a hospital or physician office) to order tests, retrieve and store statistical data or status the progress of previously ordered tests, and at least one labsite computer for receiving physician requests for tests and reporting their results. The physician computer and labsite computer are interconnected by a computer network. The physician computer receives a physician or user request for ordering a test, causes a test request message to be sent to the labsite computer, causes a request for statistical data to be sent to the network, and receives statistical data from the network. The labsite computer is programmed to receive a test request message and to cause a test results message or a test status message to be sent to the physician computer.

8 Claims, 20 Drawing Sheets

| Group I | Group II | Group III | Group IV | Group V | Group VI |
|---|---|---|---|---|---|
| Basic Hematology | Urinalysis | Basic Chemistry | Special Chemistry | Microbiology | Sub Specialties |

Group 1 Basic Hematology contains profiles:

- APTT COR(1:1 DILUTION)–BL
- BLEEDING TIME
- C–REACTIVE PROT
- CBC–NO DIFF–BL
- CBC/PLATELET
- CBC/PLATELET/MAN DIFF(ACC)
- CHEM WHOLE BODY PANEL–BL
- CK MB–BL
- CPK–BL
- CULTURE–BLOOD RESINS
- EOSINOPHIL COUNT–BL
- ER–AMYLASE–BL
- ER–APTT–BL

Ordered profiles for patient CpatLastName CPatFirstN

CPK–BL

[↑] [↓]

Clear Ordered    Previous Orders    Print Order — 626

Profile CHEM WHOLE BODY PANEL–BL* contains test(s)

- ALB
- ALK PHOS
- CALCIUM
- CHOLESTEROL
- CPK
- CREATININE

- G.I. BLEEDING–536.9
- GALL BLADDER DISEASE–575.9
- GASTRITIS–535.5
- GESTATIONAL DIABETES–648.0
- GLAUCOMA–365.9

<< Back    DIS Reporting    Exit

FIG. 9

| | | | | |
|---|---|---|---|---|
| 7/24/96 | ABDOMINAL PAIN –728.0 | | | |
| 7/8/96 | PELVIC INFLAMMATORY DISEASE (PID), 614.9 | I | APTT COR(1:1 DILUTION)–BL | Just Ordered | Abram Abramovitch |
| | | IV | AMOEBA ANTIBODY SCREEN–BL | Result pending | Valodya Pystibrator |
| | | IV | ANTITHYROID ANTIBODY–BL | Result pending | |
| | | IV | CATECHOLAMINES TOTAL–BL | Result pending | |
| | | IV | DIAZEPAM(VALIUM)–BL (INCINOR | Result pending | |
| | | VI | ANTIBODY IDENTIFICATION | Result pending | |
| | | VI | MISC BLOOD BANK ORDER AO | Result pending | |
| | | VI | TRANS REACTION WKUP W/REPT | Result pending | |
| 7/7/96 | ASTHMA – 493.8 | VI | ANTIBODY IDENTIFICATION | Just Ordered | Abram Abramovitch |
| | | VI | ORDER PLATELETS PHERISIS | Just Ordered | |
| | | VI | TRANS REACTION WKUP W/REPT | Just Ordered | |
| 7/7/96 | ARTERIOSCLEROTIC HEART DISEASE – 414.9 | II | KETONE URINE | Result pending | Abram Abramovitch |

Now you see Order from  8/4/96  Doctor  Cinch Clach  Diagnosis  636.8

<< Back        Print this Order        Exit DIS Test Ordering

DIS REPORTER
File  Help

DIS CUMULATIVE TEST RESULTS

Roger Williams Hospital

Pt. name: DORIS                D/A    4/3/94
Age/Sex: 75  Female            Acct#  600125124
Physician:                     Date:  22-FEB-97

I. BASIC HEMATOLOGY

COULTER

| | | WBC | RBC | HgB | Hct | Plat | MCV | MCH | MCHC | mpv |
|---|---|---|---|---|---|---|---|---|---|---|
| | | 10n3 | 10n6 | GM% | % | 10n3 | FL | PG | % | |
| ref. range | | 3.5 | 3.50 | 11.5 | 33.5 | 15.0 | 50.0 | 27.0 | 32.0 | |
| Date | Time | 11.0 | 5.20 | 15.5 | 46.5 | 45.0 | 100.0 | 34.0 | 37.0 | |
| 7/5/94 | 7:30 | 12.2+ | 3.86 | 11.6 | 35.9 | 234 | 93.0 | 30.1 | 32.3 | |
| 7/7/94 | 10:24 | 15.8+ | 3.93 | 11.8 | 36.9 | 194 | 93.9 | 30.0 | 32.0 | |
| 7/8/94 | 7:00 | 12.8+ | 3.96 | 11.9 | 37.6 | 202 | 94.9 | 30.1 | 31.6- | |
| 7/9/94 | 7:00 | 9.9 | 4.06 | 12.1 | 38.6 | 213 | 95.1 | 29.8 | 31.3- | |

Page: 1

FIG. 18

DIS CUMULATIVE TEST RESULTS
ROGER WILLIAMS HOSPITAL

PT. NAME  CONEY DORIS    D/A      D4/3/94
AGE/SEX   75 FEMALE      ACCT#    600125124
PHYSICIAN                DATE:    1-MAY-97

1. BASIC HEMATOLOGY

| HEMOGRAM: | WBC | RBC | Hgb | Hct | Plat | MCV | MCH | MCHC | MPV | RDWCV |
|---|---|---|---|---|---|---|---|---|---|---|
| | 10n3 | 10n6 | GM% | % | 10n3 | FL | PG | % | | |
| Ref.range | 3.5 | 3.80 | 11.5 | 33.5 | 150 | 80.0 | 27.0 | 32.0 | | |
| | 11.0 | 5.20 | 15.5 | 46.5 | 450 | 100.0 | 34.0 | 37.0 | | |

| Date | Time | | | | | | | | | |
|---|---|---|---|---|---|---|---|---|---|---|
| 7/5/94 | 7:30 | 12.2+ | 3.86 | 11.6 | 35.9 | 234 | 93.0 | 30.1 | 32.3 | |
| 7/7/94 | 10:24 | 15.8+ | 3.93 | 11.8 | 36.9 | 194 | 93.9 | 30.0 | 32.0 | |
| 7/8/94 | 7:00 | 12.8+ | 3.96 | 11.9 | 37.6 | 202 | 94.9 | 30.1 | 31.6- | |
| 7/9/94 | 7:00 | 9.9 | 4.06 | 12.1 | 38.6 | 213 | 95.1 | 29.8 | 31.3- | |
| 7/10/94 | 7:00 | 7.6 | 4.17 | 12.5 | 39.8 | 195 | 95.4 | 30.0 | 31.4- | |
| 7/11/94 | 7:00 | 11.3+ | 4.34 | 13.0 | 41.7 | 218 | 96.1 | 30.0 | 31.2- | |
| 7/12/94 | 7:00 | 12.6+ | 4.05 | 12.2 | 38.8 | 217 | 95.8 | 30.1 | 31.4- | |
| 7/13/94 | 7:00 | 11.3+ | 3.89 | 11.5 | 37.7 | 195 | 96.9 | 29.6 | 30.5- | |
| 7/14/94 | 7:00 | 13.9+ | 4.15 | 12.5 | 39.4 | 218 | 94.9 | 30.1 | 31.7- | |
| 7/15/94 | 10:29 | 12.8+ | 4.12 | 12.4 | 38.4 | 224 | 93.2 | 30.1 | 32.3 | |
| 7/16/94 | 7:00 | 13.5+ | 4.01 | 12.0 | 37.2 | 223 | 92.8 | 29.9 | 32.3 | |
| 7/17/94 | 7:00 | 13.4+ | 3.86 | 11.5 | 35.7 | 213 | 92.5 | 29.8 | 32.2 | |
| 7/19/94 | 7:00 | 14.9+ | 4.39 | 13.3 | 40.0 | 275 | 91.1 | 30.3 | 33.3 | |
| 7/21/94 | 7:00 | 14.6+ | 4.03 | 12.2 | 36.9 | 307 | 91.6 | 30.3 | 33.1 | |

| DIFF/MORPH: | Polys | Bands | Lymph | Mono | Eos | Baso | RBC | PLAT | other | comm |
|---|---|---|---|---|---|---|---|---|---|---|
| Ref.range | 45 | 0 | 20 | 1 | 0 | 0 | | | 0 | |
| | 65 | 10 | 45 | 10 | 3 | 2 | | | 0 | |

| Date | Time | | | | | | | | | |
|---|---|---|---|---|---|---|---|---|---|---|
| 7/5/94 | 7:30 | | | 16- | 3 | 1 | | NL | | |
| 7/7/94 | 10:24 | 81+ | 5 | 9- | 5 | | | NL | | |
| 7/8/94 | 7:00 | | | 8- | 4 | 1 | | (1) | | (2) |
| 7/9/94 | 7:00 | | | 12- | 3 | 1 | | NL | | |
| 7/10/94 | 7:00 | | | 20 | 4 | 1 | 1 | NL | | |
| 7/11/94 | 7:00 | | | 14- | 3 | 1 | 0 | (3) | | (4) |
| 7/12/94 | 7:00 | | | 23 | 4 | 1 | | NL | | |
| 7/13/94 | 7:00 | | | 16- | 5 | 1 | 0 | (5) | | (6) |
| 7/14/94 | 7:00 | | | 18- | 4 | 0 | 0 | NL | | |
| 7/15/94 | 10:29 | 77+ | 1 | 13- | 7 | 1 | | NL | | |
| 7/16/94 | 7:00 | | | 16- | 5 | 2 | | (7) | | (8) |
| 7/17/94 | 7:00 | | | 15- | 4 | 1 | | NL | | |
| 7/19/94 | 7:00 | 83+ | | 10- | 5 | | | NL | | |

FIG. 20

INTEGRATED SYSTEM AND METHOD FOR ORDERING AND CUMULATIVE RESULTS REPORTING OF MEDICAL TESTS

This application claims the benefit of U.S. Provisional Patent Application Ser. No. 60/041,853 filed Apr. 9, 1997.

FIELD OF THE INVENTION

This invention relates to an improved system and method for on-line ordering of medical tests in a health care network, an improved system and method for uniformly recording and reporting test results, and an improved system and method for collecting and statistically analyzing test results.

BACKGROUND OF THE INVENTION

Diagnosis, treating and preventing human illness is one of the most information-intensive of all intellectual activities. However, less than 5% of U.S. physicians are currently using computers for clinical purposes. Providers often do not have or cannot find the information they need to respond quickly and appropriately to patient medical problems. Information of value is not widely shared, and paper output of existing systems must be manually collated in what is called a Patient Medical Record (PMR) or "chart." That portion of the PMR which contains clinical data is referred to as the Clinical Patient Record (CPR). The paper-based patient medical record can be in only one place at a time.

Health care providers, payers, information system vendors, and state governments have teamed to plan and build Health Information Networks (HINs) in at least 11 states. Simultaneously, a host of large corporations have constructed proprietary HINs for processing clinical Electronic Data Interchange (EDI) transactions, including both data and images such as x-rays. These attempts to provide informational interchange have involved all sectors of the industry. Also, the proliferation of the global network commonly referred to as the "Internet" has been used to exchange information between different entities in the health care community. Thus far, these system have been primarily limited to very specialized health care applications. For example, U.S. Pat. No. 5,715,823 discloses a medical ultrasonic diagnostic imaging system capable of being accessed over the Internet, making ultrasonic images, diagnostic reports, and ultrasound diagnostics information and operation accessible to a conventional PC.

While other databases created by health care service providers and medical equipment suppliers are available, access is usually limited. Typically, many systems require the payment of a fee or participation in a restricted organization in order to gain authority to utilize the database. Many others available on the Internet are limited in terms of features and services provided. The strong forces of market-oriented health care reform, the accelerating growth of managed care plans and capitated payment necessitate the automation and re-engineering of the labor intensive, paper-based processes associated with the medical profession.

One barrier to implementation of these networks has been resistance by practicing physicians. Many physicians are computer-phobic and resistant to change in their practice methods. There is an industry-wide consensus that physicians will routinely use hospital and office computers only when they become easy to use and when they provide significant applications that save time, improve productivity, and streamline the patient care process.

Another barrier to effective operation of such community health networks has been an inability to electronically transfer patient test records between a variety of geographically dispersed offices and display them in an effective standardized format. Many smaller clinical laboratories still mail office test results to doctors. The larger labs deliver results of individual tests by courier, fax, or using an on-site printer. Relying on paper, fax and phones for reporting this information significantly reduces productivity and increases costs throughout the health care field. No U.S. hospital or freestanding clinical lab yet reports results of the billions of biochemical and microbiology tests to doctors in a standardized and integrated format.

U.S. Pat. No. 4,315,309 to Robert Coli, M.D. discloses an integrated medical test data storage and retrieval system for use in a single facility such as a hospital, as shown in FIG. 1. Test request 2 is generated by a physician or other medical personnel and entered into the system through test request entry terminals 4 placed throughout the hospital. The test request is forwarded to test request compiler 6 for storage in a test request file 8, which periodically generates specimen pickup lists 10 which are distributed to wards in the hospital. Body fluids or tissue samples are forwarded to laboratory 12 in individual specimen containers 14. The tests are performed in laboratory 12 in accordance with a work profile generated on profile sheets 16. The results are recorded and entered at entry terminal 18, and forwarded to patient result compiler 20 for storage in a patient result file 22. Compiler 20 generates a ward report 24 listing tests in progress for that ward, and a diagnostic data system patient lab report 26 which is formatted to provide cumulative results reporting. With this reporting format, the test results are presented by assigning a vertical column of the page or display screen to each test, and a horizontal row to each date and time that tests were performed. In this manner, the information for each patient is presented concisely and in a manner that facilitates effective problem diagnosis.

However, as can be seen, this early system was designed to operate within a single large hospital facility, and does not provide any ability to place test orders or receive test data over a network. For example, the disclosed system does not connect a doctor's office to an outpatient laboratory or clinic where patients may be sent for lab work, and does not facilitate selection of a particular laboratory from those that may be capable of performing a specific test.

Other clinical data processing systems are provided in U.S. Pat. Nos. 3,872,448 to Mitchell, Jr., 5,099,424 to Schneiderman, 5,262,943 to Thibado et al., 5,551,022 to Tariq et al., 5,265,010 to Evans-Paganelli et al., 5,262,944 to Weisner et al., 5,072,383 to Brimm et al., 5,392,209 to Eason et al., 5,327,341 to Whalen et al., 5,549,117 to Tacklind et al., 5,277,188 to Selker, and 5546,580 to Seliger et al. However, arrangements of the types disclosed in these references similarly fail to provide medical practitioners with an optimal networked test ordering and results reporting system.

Thus, there is a need for an improved networked computer system that provides integrated electronic test selection and results reporting, with the tests organized in a consistent and easy-to-understand manner for both selection of the tests to be performed, and reporting of the results. There is also a need for a system that provides effective communication of test orders and results between a physician's office and a remote laboratory. Moreover, there is a need for a system of this type that will identify for the physician the local laboratories capable of performing a specific test, and permit selection among those laboratories and appropriate transmission of the test order, preferably over the Internet.

SUMMARY OF THE INVENTION

Therefore, it is a general objective of the present invention to provide an improved networked computer system for integrated electronic test selection and results reporting.

Another objective of the present invention is to provide a test ordering module that organizes tests in meaningful clinical groupings (e.g. 5 groups such as basic hematology, urinalysis, basic chemistry, special chemistry, and microbiology).

A further objective of the invention is to provide a clinical test ordering and results reporting system wherein other layers of data may be attached to the test result output. For example, by clicking on a test, the user may retrieve a clinical description of the test or demographic information.

Another objective of the invention is to provide a clinical test ordering and results reporting system wherein drug advertising is inserted in the output, with a particular displayed ad triggered by abnormal clinical results.

It is also an objective of the invention to provide a clinical test results reporting system in which a physician workstation performs record merging by connecting to various labs and hospitals in sequence to obtain updated information and create a complete patient record.

Another significant objective of the invention is to provide a test ordering system that determines which labs perform the desired test, selects that lab's name, checks for HMO or insurance authorization, and directs the patient. The system preferably provides access to various labs.

It is also an object of the invention to provide a test ordering and results reporting system that permits patient record exchange between physicians for referrals, second opinions, etc. A central data respository may be provided to permit exchange between mini-labs.

Another objective of the invention is to provide a system that provides data and demographic information such as live public health statistics through a single query across multiple hospitals.

These objectives and many others which will be apparent on review of the specification, drawings, and claims are achieved in the present invention by linking each physician's office to a plurality of remotely located laboratories, and providing communication of test orders and results with each lab. The available tests are organized in meaningful clinical groupings which are consistent for both selection of the tests to be performed, and reporting of the results.

The system receives a selection of the desired tests, and also a diagnosis code associated with the test. A list of diagnosis codes is integrated into the ordering module. The system then automatically identifies for the physician the local laboratories capable of performing the needed tests, checks for HMO or other controlling authorization, permits selection among those laboratories, transmits the test order, and provides printed directions and written confirmation for the patient. Thus, the system provides electronic access to multiple labs, in contrast to hospital proprietary terminals.

Following performance of the tests, the results are transmitted from the laboratory in a data stream formatted for cumulative results reporting, and displayed for the physician with an organization identical to the organization of the tests within the ordering function. This organization indexes and organizes the test results to facilitate analysis and rapid recognition of clinical patterns and trends to facilitate accurate diagnosis.

The test results are aggregated with previous test results in a patient record, which may be compiled at the physicians office, or in a central CHIN (Community Health Information Network) computer system. The system facilitates patient record collection by a physician who has not seen the patient previously, for referrals, second opinions, etc. without requiring a central repository or that records be collected and transferred from another physician's office.

In a peer-to-peer network embodiment, to compile a patient record in real time, the physician workstation may perform record merging by connecting to labs, hospitals, and CHIN record repositories in sequence to obtain full updated information for the patient.

All test results for the patient are displayed for the physician in a cumulative results reporting format to highlight changes in the results of the same test over time for that patient. Where text information or "notes" are associated with a particular test result, an on-screen indication is provided at the test result, and the notes are accessible on-screen via a hyperlink accessed by clicking on the test result. Test results are displayed on screen with visual aids for identifying values outside a normal range, such as color coding of the text or background and the use of different fonts.

Other layers of data may be attached to the test result output. For example, by clicking on a test, the user may retrieve a clinical description of the test or demographic information. The software provided for the physician's office may include a clinical notes recording feature and a voice control feature.

Advertising for particular drug treatments or medical devices that may be needed by the patient may be provided as part of the test results reporting output. In particular, displayed drug advertising may be selected based on drugs which are recommended treatments for abnormal clinical results of a particular test. Preferably, the drug treatment advertisement is hyper-linked to full advisory information about the drug, so that the physician can readily obtain information about that possible treatments for conditions suggested by the test results.

Another significant feature of the system is its ability to provide aggregated data and demographic information (with or without patient identification), creating "live" public health statistics through a single query across multiple hospitals, clinics, labs, and offices. This broad-based information will be useful to HMOs in cost prediction.

In one preferred embodiment, the network according to the present invention comprises a plurality of personal computers each of which are logically connected to an intermediate computer which may be connected to a database computer. File and resource serving functions are provided transparently to users. The network scheduler collects requests from all computers associated with the network scheduler and satisfies them either by immediately processing the request internally or by routing the request to the patient database computer. This embodiment enhances communication among differing segments of the health care profession by providing a system and method for ordering and cumulative results reporting of medical tests through a remote terminal interacting over a telephone line or other network connection with a host computer. In its preferred embodiment, the system offers readily available online access to databases containing patient, laboratory, and medical testing information; online report generation capabilities; online product information; and automatic billing for services performed.

In one aspect, the invention features a network-based test ordering and results reporting system that includes at least one network scheduler, at least one patient database computer, at least one hospital computer for operation by a physician or other medical specialist working in a hospital, at least one lab site/subspecialty computer for operation by a lab technician, at least one physician computer for operation by a physician or other medical specialist working in a private clinic, and at least one insurer computer for operation by an insurance claims agent. The network scheduler, patient database computer, hospital computer, lab site/subspecialty computer, physician computer, and insurer computers are interconnected by a computer network. The patient database computer is programmed to: (1) receive an access message containing the patient ID, test ID, lab ID (optional) and logon ID from a hospital computer or a physician computer; (2) evaluate an access message to determine whether a requesting computer is authorized to request/perform the particular task; (3) cause a message to be communicated to the patient's indemnity insurer requesting authorization to perform the test; (4) select an appropriate lab to conduct the test (if necessary); (5) receive an access message from the patient's indemnity insurer either authorizing or disapproving the request for indemnification; (6) cause a message to be sent to the requesting computer informing the requester of the insurance company's decision; (7) cause a message that comprises the patient ID, patient's insurance carrier, diagnosis, and test ID to be communicated to the lab that is to conduct the test; and (8) cause a message to be communicated to the patient informing him/her of the test, location, special instructions, etc. The hospital and physician computers are programmed to: (1) receive a user request for a laboratory test; (2) identify a candidate laboratory that is qualified to conduct the test (optional); (3) cause an access message to be created that comprises the patient ID, patient's insurance carrier, diagnosis, test ID, lab ID (optional), and logon ID; (4) cause the access message to be sent to a mainframe patient database computer. The lab site/subspecialty computer is programmed to: (1) receive an access message containing the patient ID, test ID, diagnosis, and logon ID from a patient database mainframe requesting a lab test; (2) receive an access message containing the patient ID, test ID, and logon ID from a patient database computer that authorizes the lab to conduct the test; and (3) cause a message to be communicated to the lab technician to conduct the test. The insurer computer is programmed to: (1) receive an access message requesting authorization to conduct a test from a mainframe patient database computer containing a patient ID, test ID and the diagnosis; (2) cause an access message to be created that comprises the patient ID, hospital ID, test ID, authorization code, and logon ID; (3) cause the access message to be sent to the mainframe patient database computer either authorizing or denying payment for the requested test. To aid the physician or other medical specialist in completing the access message, a list of diagnosis codes is integrated into the ordering module. Following performance of the tests, the results are transmitted from the laboratory in a data stream formatted for cumulative results reporting, and displayed for the physician with an organization identical to the organization of the tests within the ordering function. This organization indexes and organizes the test results to facilitate analysis and rapid recognition of clinical patterns and trends to facilitate accurate diagnosis.

The test results are aggregated with previous test results in a patient record, which may be compiled at the physician's office, or in a central HIN (Health Information Network) computer system. The system facilitates patient record collection by a physician who has not seen the patient previously, for referrals, second opinions, etc. without requiring a central repository or that records be collected and transferred from another physician's office.

The invention provides a simple design architecture for the network-based test ordering and results reporting system that allows the patient database computer to respond to test requests from the hospital and physician computers without the patient database computer having to store information in a database regarding which physicians and medical specialists are permitted to request such tests and which insurer's are permitted to authorize such tests. In this case, when a patient database computer receives a request to conduct a test, the patient database computer need only check the access message from the hospital or physician computer to ensure it was created by a hospital or physician computer (thereby establishing for the patient database computer that the requester is permitted to request the test), check the access message from the insurer computer to ensure that it was created by an insurer computer (thereby establishing for the patient database computer that the requester is permitted to authorize the test) and then the patient database computer can cause a message to be communicated to a lab technician to conduct the test.

In another aspect, the invention features a network-based test ordering and reporting system that includes at least one network scheduler, at least one patient database computer, at least one hospital computer for operation by a physician or other medical specialist working in a hospital and at least one lab site/subspecialty computer for operation by a lab technician. The network scheduler, patient database computer, hospital and lab site/subspecialty computers are interconnected by a computer network. The mainframe patient database computer is programmed to: (1) receive an access message containing patient database modifications from a hospital or lab site/subspecialty computer; (2) evaluate an access message to determine whether a requesting computer is authorized to modify the patient database; and (3) modify the patient database in response to a hospital computer and lab site/subspecialty computer access message. The hospital and lab site/subspecialty computers are programmed to: (1) receive direct user input to modify the patient database; (2) create an access message that comprises the patient ID, test ID, logon ID and updated database information; and (3) cause the access message to be sent to the patient database computer for eventual placement in the patient database.

In another aspect, the invention features a network-based test ordering and reporting system that includes at least one network scheduler, at least one mainframe patient database computer, at least one hospital computer for operation by a physician or other medical specialist working in a hospital, a physician computer for operation by a physician or other medical specialist working in a private clinic, and a lab site/subspecialty computer for operation by a lab technician. The network scheduler, patient database computer, hospital, physician and lab site/subspecialty computers are interconnected by a computer network. The mainframe patient database computer is programmed to: (1) receive an access message containing a request for updated test status information; (2) evaluate an access message to determine whether a requesting computer is authorized to receive updated status information; and (3) transmit the latest version of the test information to the hospital, physician, or lab site/subspecialty computers. The hospital, physician and lab site/subspecialty computers are programmed to: (1) receive user input that requests updated test status information; (2) create an access message, reflecting the user request for updated test status information; (3) cause the access message to be sent to the patient database computer; and (4) display the updated information.

In another aspect, the invention features a network-based test ordering and results reporting system that includes at least one network scheduler, at least one mainframe patient database computer, at least one hospital computer with a patient database connected to the hospital computer for operation by a physician or other medical specialist working in a hospital, at least one lab site/subspecialty computer for operation by a lab technician, at least one physician computer for operation by a physician or other medical specialist working in a private clinic, and at least one insurer computer for operation by an insurance claims agent. The network scheduler, patient database computer, hospital, physician, lab site/subspecialty and insurer computers are interconnected by a computer network. The mainframe patient database computer is programmed to: (1) receive an access message containing a user request for a particular report; (2) evaluate an access message to determine whether a requesting computer is authorized to receive the requested information; and (3) transmit the requested information to the hospital, physician, lab site/subspecialty, or insurer computers. The hospital, physician, lab site/subspecialty and insured computers are programmed to: (1) receive user input requesting a report; (2) create an access message, reflecting the user request for a specific report; (3) cause the access message to be sent to the patient database computer; and (4) display the updated information.

In another aspect, the invention features a hypertext statement system that includes a client computer for operation by a client user and one or more server computers for operation by a server user. The client computer and the server computers are interconnected by a computer network. At least one of the server computers is programmed to record advertising information records for particular drug treatments and medical devices that may be needed by a patient. Each of the advertising information records includes full advisory information about the drug treatments or medical devices, so that the physician can readily obtain information about possible treatments for conditions suggested by the test results. The server computer is programmed to transmit a statement document that includes the advertising information records to the client computer. The client computer is programmed to display the advertising and product information, to receive a request from the client user to display the advertising and product information, and to cause an advertisement and product information hypertext link derived from an advertising information record to be activated. At least one of the server computers is programmed to respond to activation of the product hypertext link by causing the information to be sent to the client computer.

In another aspect, the invention features a hypertext statement system that includes a client computer for operation by a client user and one or more server computers for operation by a server user. The client computer and the server computers are interconnected by a computer network. At least one of the server computers is programmed to store patient test data records in a database. Each of the patient test data records includes a patient ID, test ID, date, observed values, and additional "notes". The server computer is programmed to transmit a statement document that includes the patient test data records to the client computer. The client computer is programmed to display the patient test data records with visual aids for identifying values outside a normal range, to receive a request from a client user to display test data corresponding to a data retrieval query input by the client user, and to cause a product hypertext link derived from a patient test data retrieval request to be activated. At least one of the server computers is programmed to respond to activation of the test data request by causing the data to be sent to the client computer. This feature permits the system to provide aggregated data and demographic information (with or without patient identification), creating "live" public health statistics through a single query across multiple hospitals, clinics, labs, and offices. This broad-based information will be useful to HMOs in cost prediction. Other layers of data may be attached to the test result output. For example, by clicking on a test, the user may retrieve a clinical description of the test or demographic information. The software provided for the physician's office may include a clinical notes recording feature and a voice control feature.

BRIEF DESCRIPTION OF THE DRAWINGS

FIG. 5 is a patient data entry screen used by the physician;

FIG. 7 is the test profile entry screen of FIG. 6 showing selection of a bank of tests and an associated diagnosis code;

FIG. 9 is a test ordering history display;

FIG. 18 is a screen display of test data in cumulative results reporting format according to the present invention;

FIG. 20 is an example of a test results display in a preferred embodiment.

DETAILED DESCRIPTION OF THE PREFERRED EMBODIMENTS

The present invention provides an improved networked computer system for integrated electronic test selection and results reporting. The novel concepts in the invention will be described with reference to a plurality of embodiments, beginning with the embodiment shown in FIG. 2.

Figure 1:
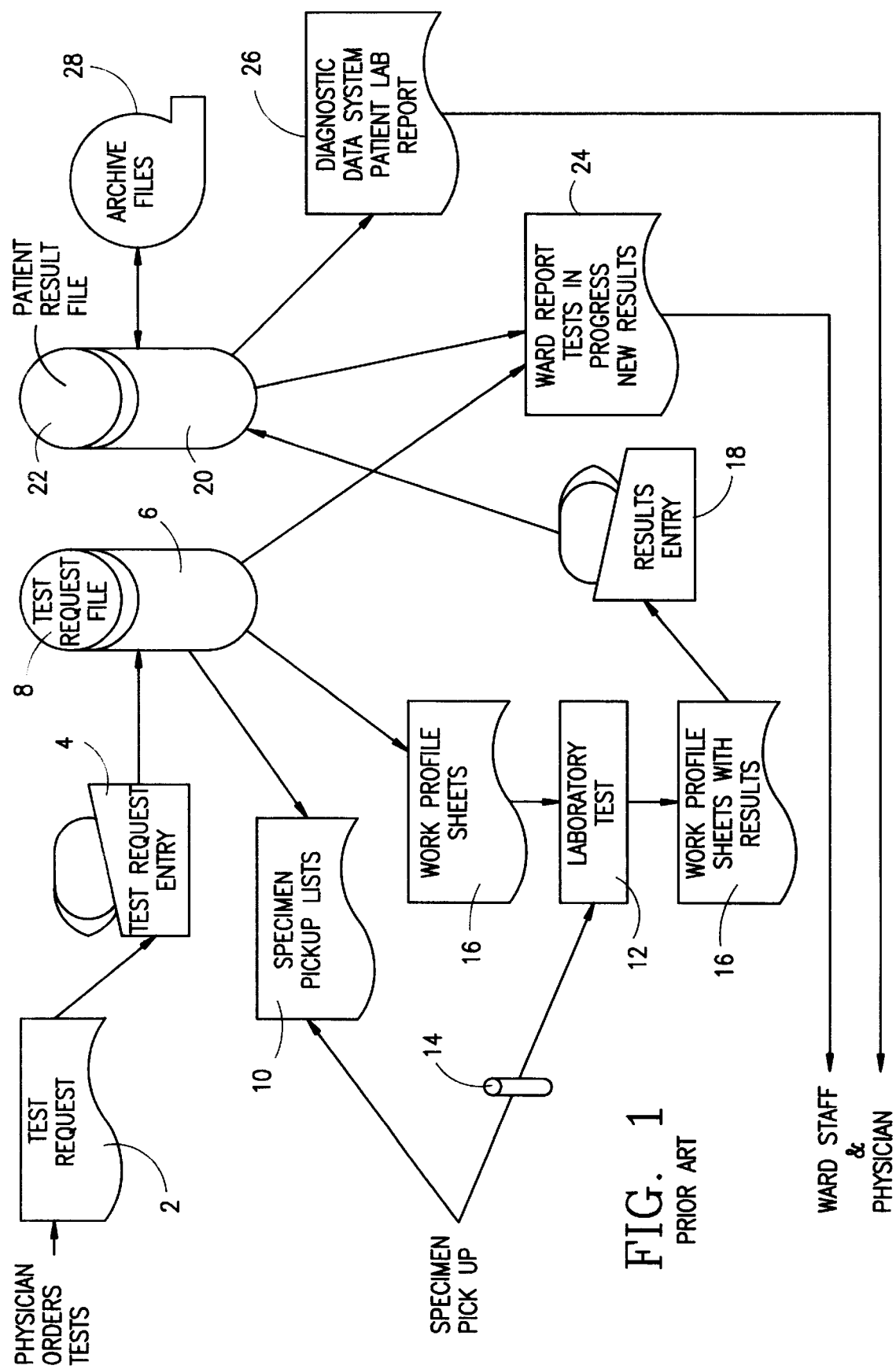
FIG. 1 is a block schematic diagram showing a conventional standalone hospital test results reporting system.
Figure 2:
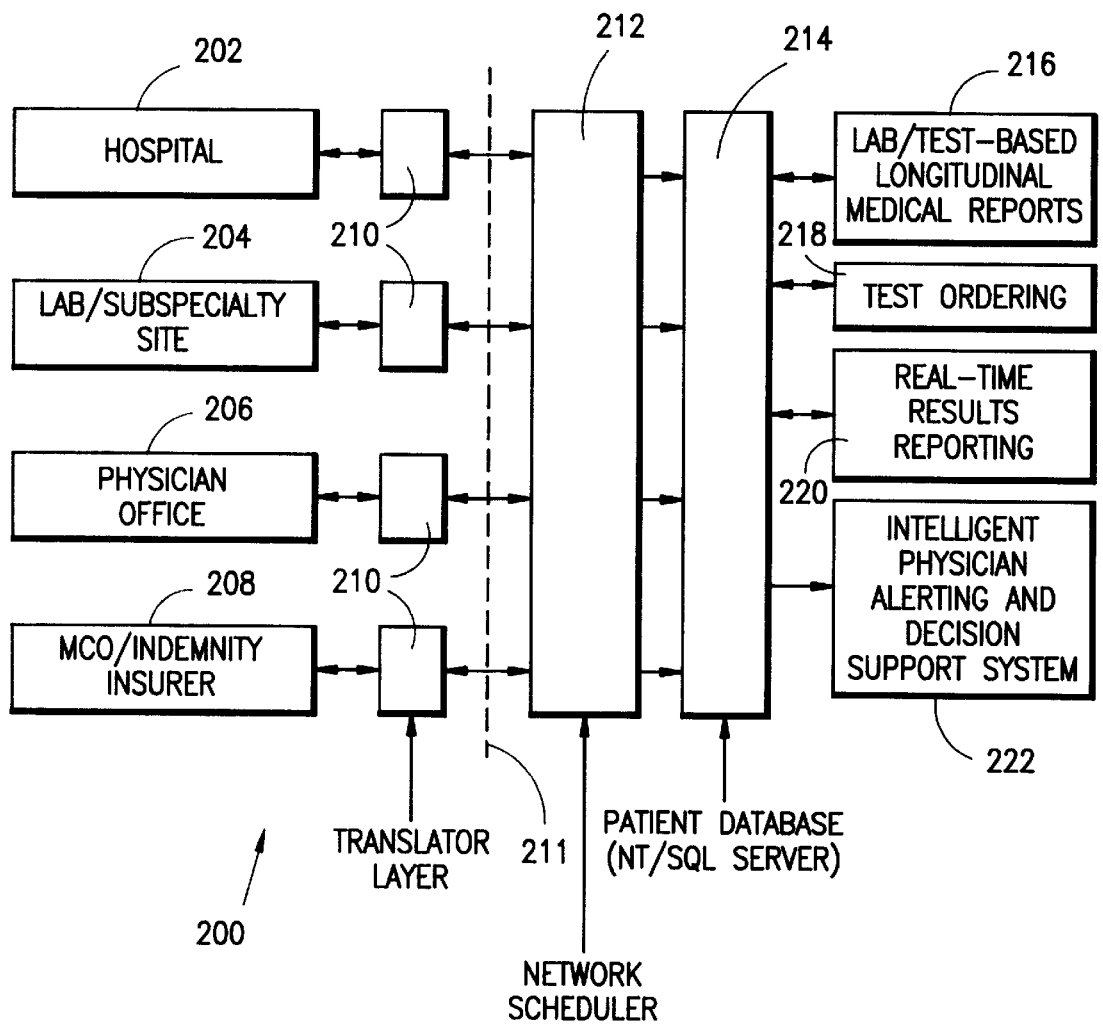
FIG. 2 is a block schematic diagram showing a distributed computing and data communications network for test ordering and results reporting according to the present invention.

FIG. 2 is a block schematic diagram showing a distributed computing and data communications network 200 for medical test ordering and results reporting according to the present invention. Network 200 includes hospital computer 202 operated by a physician or other medical specialist, a labsite computer 204 typically operated by a lab technician, a physician computer 206 operated by a physician or other medical specialist, and an insurer computer 208 operated by an insurance claims agent. The hospital, labsite, physician and insurer computers are all inter-connected by a computer network 211 such as the Internet. It is preferable that the software on computers 202, 204, 206, and 208 is directly compatible with the standardized cumulative results reporting format used by patient database computer 214, so that no format translation is necessary. As a precaution, each of these computers is also provided with a translator layer 210 which selectively converts test data between any incompatible formats used on those computers, and the cumulative results reporting format compatible with the present invention. Network scheduler 212 is an interface between patient database computer 214 and the translator layers 210 of individual computers 202, 204, 206, and 208. Network scheduler 212 may be connected to computers 202, 204, 206, and 208 by any communications link or links, including for example dedicated dialup lines, a private network, and more preferably, the Internet. File and resource serving functions are provided transparently to computer users by the network scheduler. The network scheduler 212 collects requests from all computers 202, 204, 206, and 208 associated with the network scheduler and satisfies them either by immediately processing the request internally or by routing the request to the patient database computer 214 for processing. The patient database computer 214 selectively generates longitudinal medical reports 216, and performs test ordering functions 218, real time results reporting 220, and intelligent physician alerting and decision support functions 222, as appropriate in response to requests from computers 202, 204, 206, and 208.

Patient database computer 214 is preferably an IBM(TM)-compatible computer based on an Intel(TM) Pentium(TM) processor, running the Microsoft(TM) Windows NT operating system. Functions 216, 218, 220, and 222 are implemented in server software on computer 214. The physician computer 206 is preferably an IBM(TM)-compatible computer based on an Intel(TM) Pentium(TM) processor, running the Microsoft(TM) Windows 95 or Windows NT operating system, and a client software package compatible with the software on patient database computer 214 which performs functions 216, 218, 220, and 222. Similarly, the hospital computer 202, labsite computer 204, and insurer computer 208 run client software functionally compatible with the server software of computer 214. In accordance with the preferred embodiment, the patient database computer 214 is operatively connected to the Internet. In this example, the patient database computer 214 has at least a first "home page" remotely accessible by users of the system. Physicians, laboratory technicians, and insurance claims agents can access patient, testing and payment information in the manner described below.

With the system according to the invention, users can gain access over telephone and data transmission lines to the host system by contacting the network scheduler 212. As is known in the art, this contact can be established on a network such as the Internet by sending data packets to an electronic address associated with the host system.

The system operates under control of a conventional operating system. The operating system permits various application processes to be executed including a communications application which permits data transfer with various remote terminals such as those referred to above. The communications applications permit physicians, laboratory technicians, and insurance claims agents to log onto the patient database computer, update information and create reports.

The software environment further includes a data management, storage, and retrieval application that organizes the information exchanged between hospitals, laboratories and insurance carriers. This information is organized and stored within the environment of the operating system on one or more mass storage devices. The software architecture underlying the particular preferred embodiment is based upon the hypertext conventions of the World Wide Web.

Each computer 202, 204, 206, and 208 possesses a unique network log on ID and password such that when the computer logs onto the network, it will only be permitted to execute the functions normally performed by individuals at the computer's location. For example, a hospital or a physician computer will only be permitted to execute the tasks normally performed by a medical professional or physician. Simply stated, a computer logged on as a physician computer will not be permitted to report or change the results of a laboratory test. A lab site computer correspondingly, will not be permitted to order a test for a patient. It is important to note that while the lab site, insurer and physician computers all perform unique tasks, a hospital computer is capable of performing any task that is otherwise executed on the other computers. This feature allows a full-service hospital to continue to provide a full suite of services to its patients. In alternate cases, the network can be modified to authorize the hospital computer to execute any subset of tasks normally performed by the lab, physician, and insurer computers. In this first embodiment of the invention, operating features of the system and method are implemented in both the server and client computers, which work together to perform the desired functions.

Figure 3:
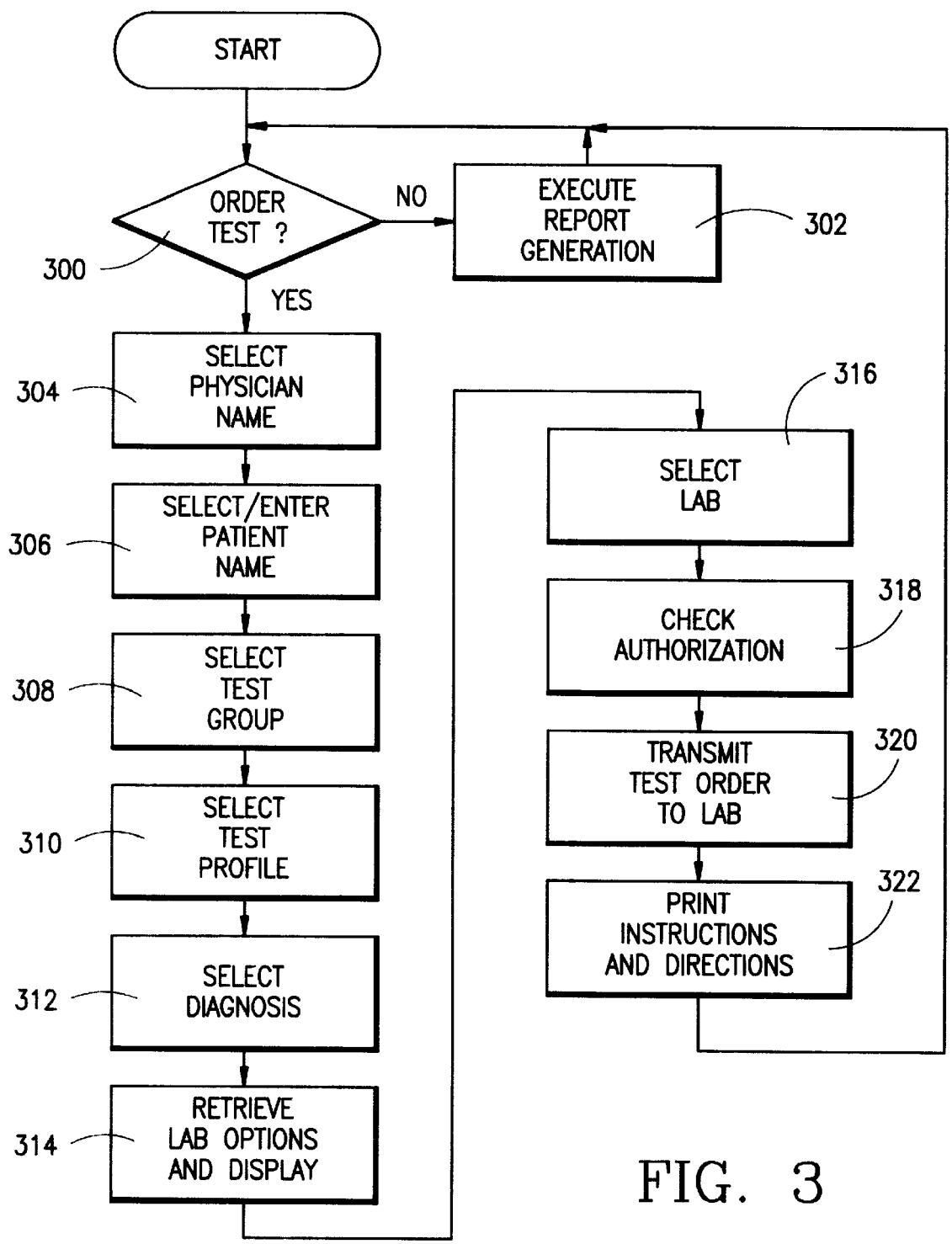
FIG. 3 is a flowchart generally describing the operation of the test ordering and results reporting system of the present invention.

With reference to FIG. 2, a medical test order begins when a physician or other medical professional at hospital computer 202 or physician computer 206 logs onto the network 211. FIG. 3 is a flowchart generally describing the operation of a hospital or physician computer's test ordering system and test results reporting system, as operable on computers 202 and 206 (shown in FIG. 2). Referring now to FIG. 3, the features of the client software include ordering medical lab tests and generating cumulative results reporting for the tests.

Figure 4:
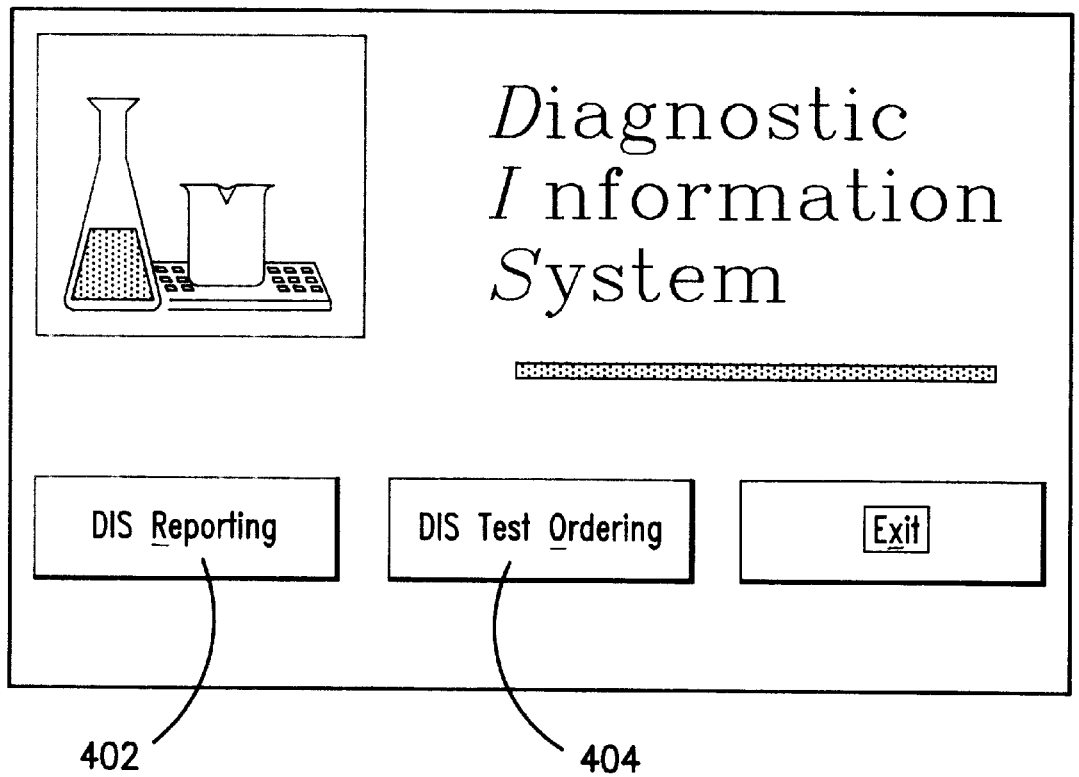
FIG. 4 is an initial screen display permitting selection of test ordering or results reporting functions of the physician interface.

Execution of the client program in FIG. 3 begins with block 300, where the program accepts input from the user to indicate whether the user wishes to order a test, or generate a report. This function is preferably performed by displaying an input screen (see FIG. 4) permitting selection of either test ordering or results reporting functions of the physician interface. The physician can click on button 402 for report generation or button 404 for test ordering (buttons shown in FIG. 4).

Referring again to FIG. 3, if test ordering is not desired, program control transfers to block 302, which executes a report generating function which will be described in more detail below. If a test is to be ordered, control transfers to block 304, where the name of the ordering physician is selected. As seen in block 304, the network first locates the physician's name and then compares the name to the physician's password, if the computer does not find a matching name or password, it denies network access to the user. After a database number of unsuccessful attempts, the network will log the hospital or physician computer off the network. If the name and password are valid, the network prompts the user to submit a request to the network 211 to schedule a test to be conducted on a particular patient.

Figure 5:
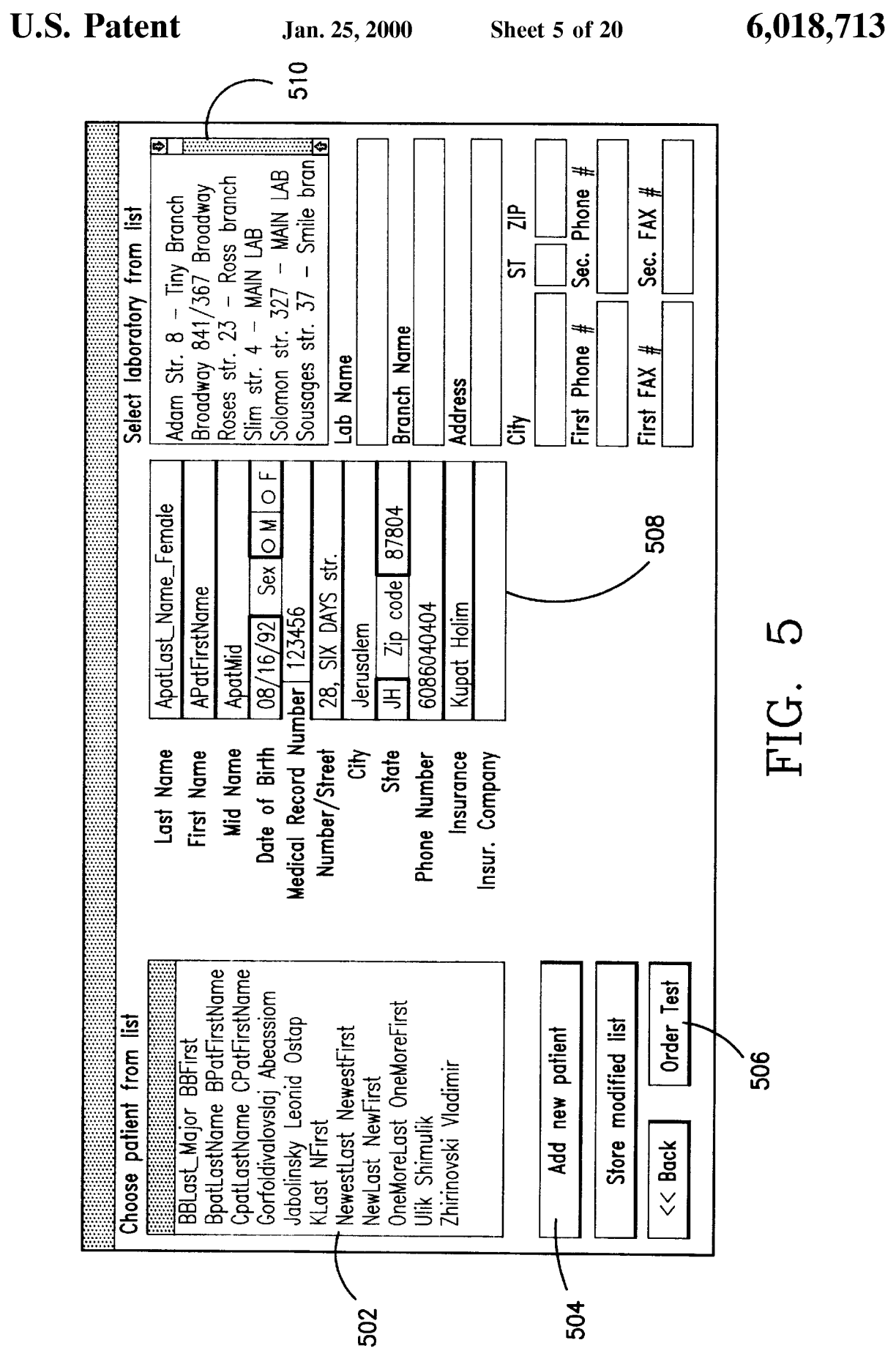

In block 306, the physician is prompted to enter the patient name. The network 211 searches the database of patient database computer 214 for a matching patient account. If it does not find a match, the network 211 sends a message back to the hospital computer 202 or the physician computer 206 indicating that an existing patient file does not exist. The network 211 then prompts the hospital or physician computer to input the patient's name again or to complete a new patient input form. This function is performed using a custom input screen as shown in FIG. 5. Existing patients may be selected from the list in scroll window 502, or the physician can select button 504 and enter data in fields 508 to add a new patient. Alternatively, the physician may select a lab to perform the test within this screen using scroll window 510. When the correct patient has been identified, the physician clicks on button 506 to continue. Clicking on button 506 transfers control to block 308 (shown in FIG. 3), where a desired test group is selected.

Figure 6:
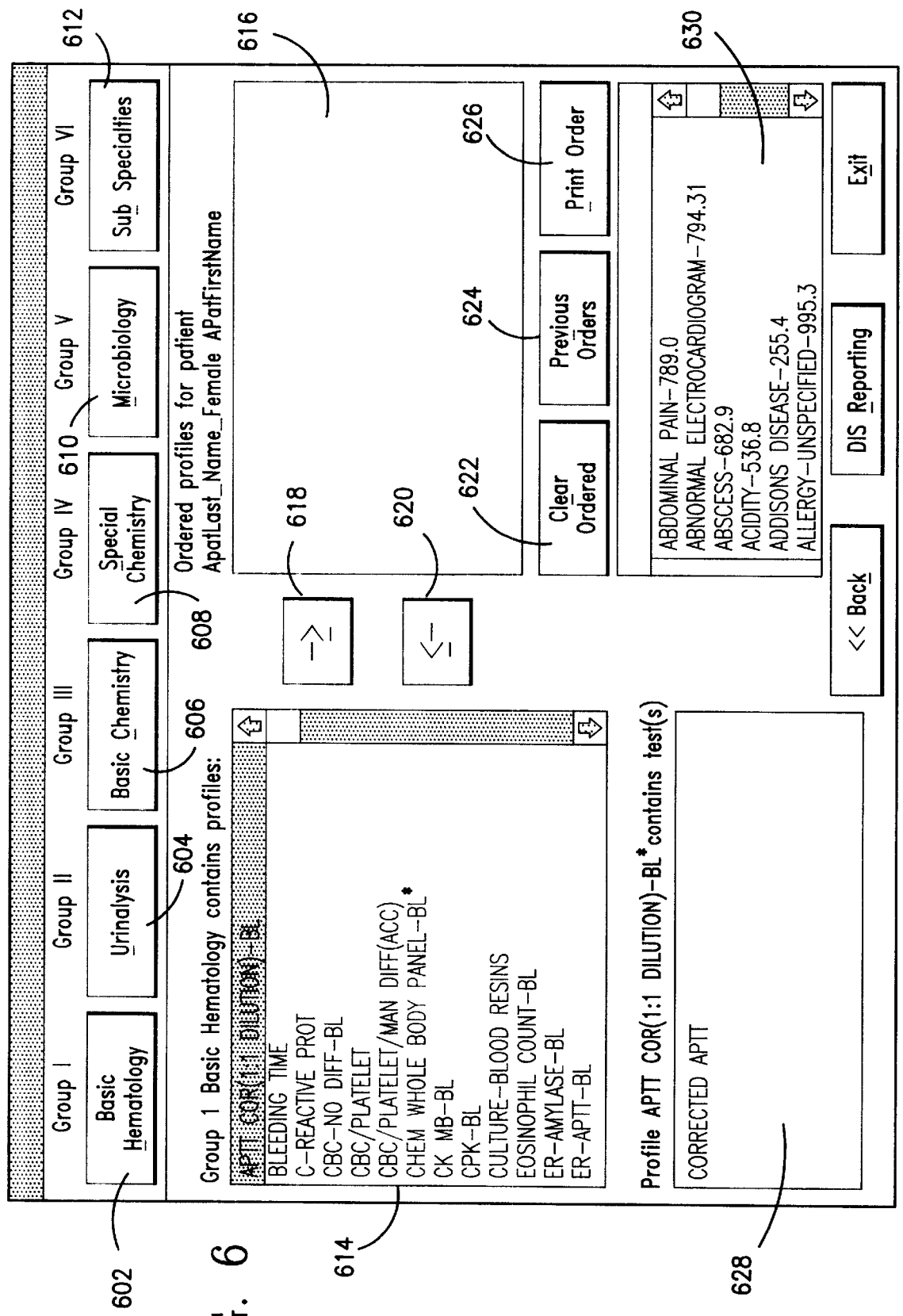
FIG. 6 is a test profile entry screen.

Referring to FIG. 6, the available tests are organized in meaningful clinical groupings which (as will be seen) are consistent for both selection of the tests to be performed, and reporting of the results.

As shown in FIG. 6, in the ordering module, individual tests are first organized into two major categories: (1) biochemical and microbiological tests, and (2) medical subspecialty tests (e.g. diagnostic radiology, multi-modality imaging, surgical pathology, cytology, cytogenetics, and blood bank). The first category is further subdivided into five groups: (1) Basic hematology, (2) urinalysis, (3) basic chemistry, (4) special chemistry, and (5) microbiology. This categorization of the test results is preferably performed according to the disclosure in U.S. Pat. No. 4,315,309, the entirety of which is incorporated herein by reference. Each of the five groups in category I, and category II, are provided with a "button" on the screen as shown in FIG. 6 at 602, 604, 606, 608, 610, and 612. To access available tests in each category, the physician clicks on the appropriate button 602–612, which then displays tests relating to that grouping in scroll window 614. As the physician orders these tests or multi-test profiles, the selected profiles are displayed in window 616. Highlighting a test profile in window 614 displays the tests included in that profile in window 628. Selection and deselection of test profiles may be made by double clicking or by selecting buttons 618 or 620. Button 622 clears the order list, button 624 displays the locally recorded order history for the patient (shown in FIG. 9), and button 626 transmits the order and/or prints the order.

The program performs a diagnosis selection function in block 312 (shown in FIG. 3). Referring again to FIG. 6, this diagnosis selection function is performed by scrolling through diagnosis selection window 630, wherein the physician selects an appropriate diagnosis code for the patient's condition to be associated with the test order. Selection of a diagnosis in this manner and association of the diagnosis with the test order facilitates authorization and ultimately payment for the test by an insurer or HMO. The possible diagnoses and associated numerical codes are preferably listed in alphabetical order in the scroll window. For non-general practice, the scroll list may be grouped by specialties or a smaller number of diagnoses most frequently used by a particular physician may be provided in the scroll list to avoid scrolling through a very large number of possible diagnoses when ordering each test. For example, a urologic surgeon would not have frequent occasion to diagnose glaucoma. Where a limited set of diagnoses are provided for ease of use, a complete set of diagnoses can be accessed by pressing an optional "more diagnoses" button on the screen (not shown) if the patient's condition is outside the limited set.

FIG. 7 shows the test profile entry screen of FIG. 6 wherein a bank of tests and an associated diagnosis code have been selected by the physician. In this example, the physician has diagnosed Gastroenteritis and has selected CPK-BL and CHEM WHOLE BLOOD PANEL-BL test profiles. The physician may then press button 626 to indicate acceptance of the test order.

Referring again to FIG. 3, following selection of the diagnosis in block 312, control passes to block 314 where lab options are retrieved and displayed for lab selection by the physician. Typically, the tests ordered by the physician will not be performed in the physician's office, but will instead be performed on a walk-in basis by an independent lab or hospital lab in the area. Before the advent of the present invention, there were no systems available for automatically permitting the selection of lab tests and diagnoses in an organized fashion, and also selection among a variety of available labs. This lab selection function facilitates selection of lab locations for performance of the test. It is considered desirable to select a lab location which participates in the patient's health care plan, is capable of performing the requested test, and is located conveniently for the patient. In block 314, the system displays appropriate labs for performing the selected tests. The lab options to be displayed may be automatically selected by the system for display on the basis of health plan participation, cost of tests, qualification to perform all selected tests, and/or location.

Figure 8:
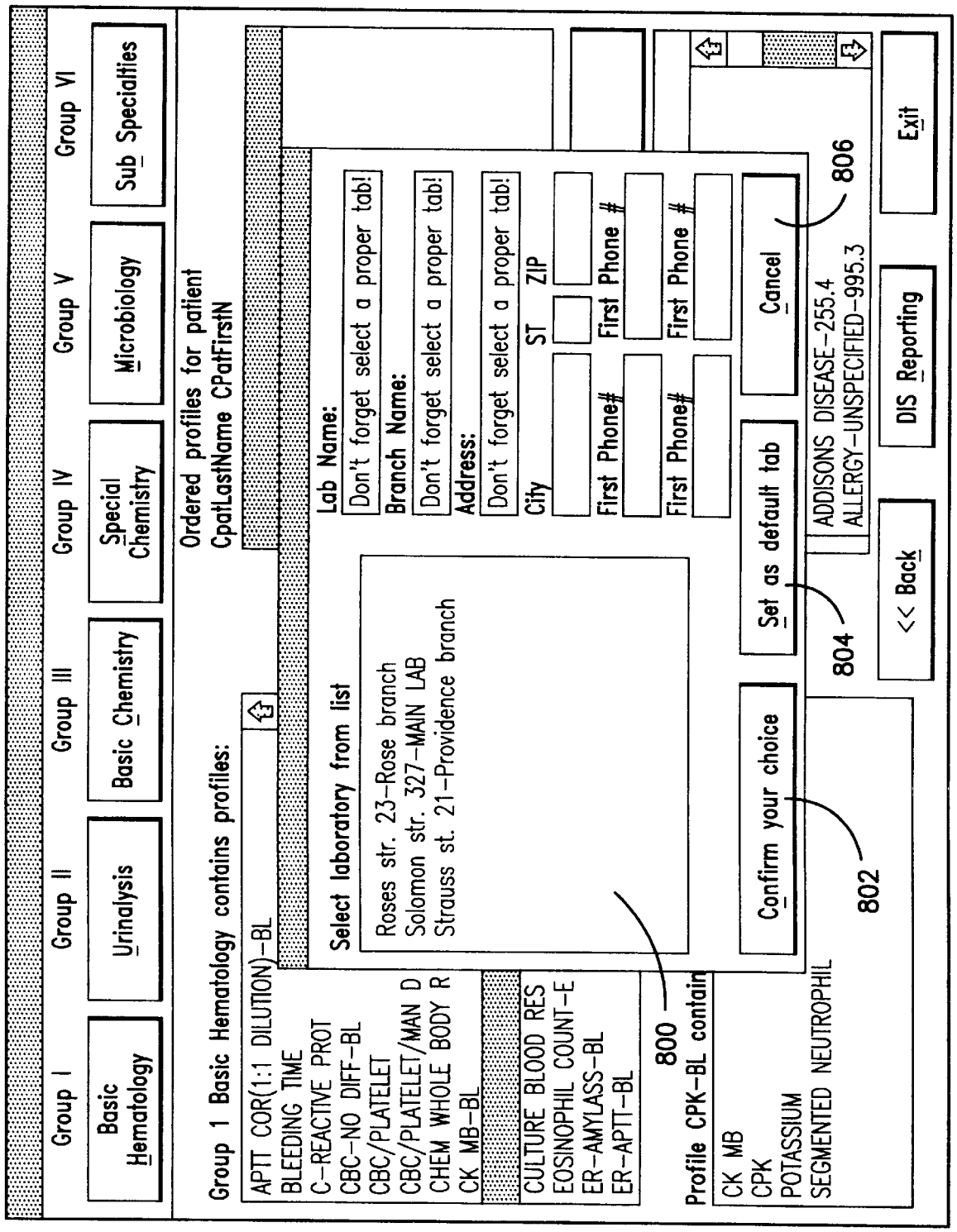
FIG. 8 is the test profile entry screen of FIGS. 6 and 7 including a lab selection menu display.

FIG. 8 shows the test profile entry screen of FIGS. 6 and 7 including a lab selection menu display 800 which is presented to the physician if no lab was previously selected. This display, along with a warning message, may also be presented if the previously selected lab is incapable of performing the tests or does not participate in the patient's health care plan.

Referring again to the flowchart of FIG. 3, after display of lab options, control passes to block 316 where the physician selects a lab by highlighting its entry and clicking on button 802 (shown in FIG. 8) to confirm the selection. Clicking button 804 (shown in FIG. 8) sets the selected lab as the default lab for future use. Selecting button 806 (shown in FIG. 8) cancels lab selection and returns the physician to the test selection screen.

After lab selection, block 318 is executed to verify authorization for the test. When authorization for a diagnostic test is requested, a test request packet or packets containing a patient name or other identifier, patient's insurance carrier, a test identifier, the preliminary diagnosis, the desired test lab and logon ID is transmitted to the patient database computer. These packets may be, for example, Internet Protocol packets.

When the patient database computer receives test request packets, it verifies whether the test request originated from an appropriate computer (i.e., physician computer or hospital computer). If not, the patient database computer sends a message to the originating computer indicating that the requesting computer is attempting to execute a task it is not authorized to perform and ignores the request. Once the patient database computer verifies that the originating computer is authorized to request a test, it sends a message to an insurer computer requesting authorization to conduct the test. Upon reading the message at his/her terminal, an insurance claims agent next determines whether the fee for the test is payable under the patient's insurance policy and if it is not, sends a message back to the patient database computer denying payment for the procedure. As shown in FIG. 3, after authorization, the final test order may be transmitted electronically to the lab in block 320, and a written test order, with patient instructions and geographic directions to the lab can be automatically printed and mailed to the patient in block 322. Thus, the system preferably links each physician's office in real time to a plurality of remotely located laboratories, either via a central server or through distributed connections, and provides almost instantaneous communication of test orders and results between physicians and labs. The system receives a selection of the desired tests, and also a diagnosis code associated with the test from the list of codes integrated into the ordering module. The system then automatically identifies for the physician the local laboratories capable of performing the needed tests, checks for HMO or other controlling authorization, permits selection among those laboratories, transmits the test order, and provides printed directions and written confirmation for the patient. Thus, the system provides automated ordering access to multiple labs, in contrast to hospital proprietary terminals which operate only within the hospital.

Figure 10:
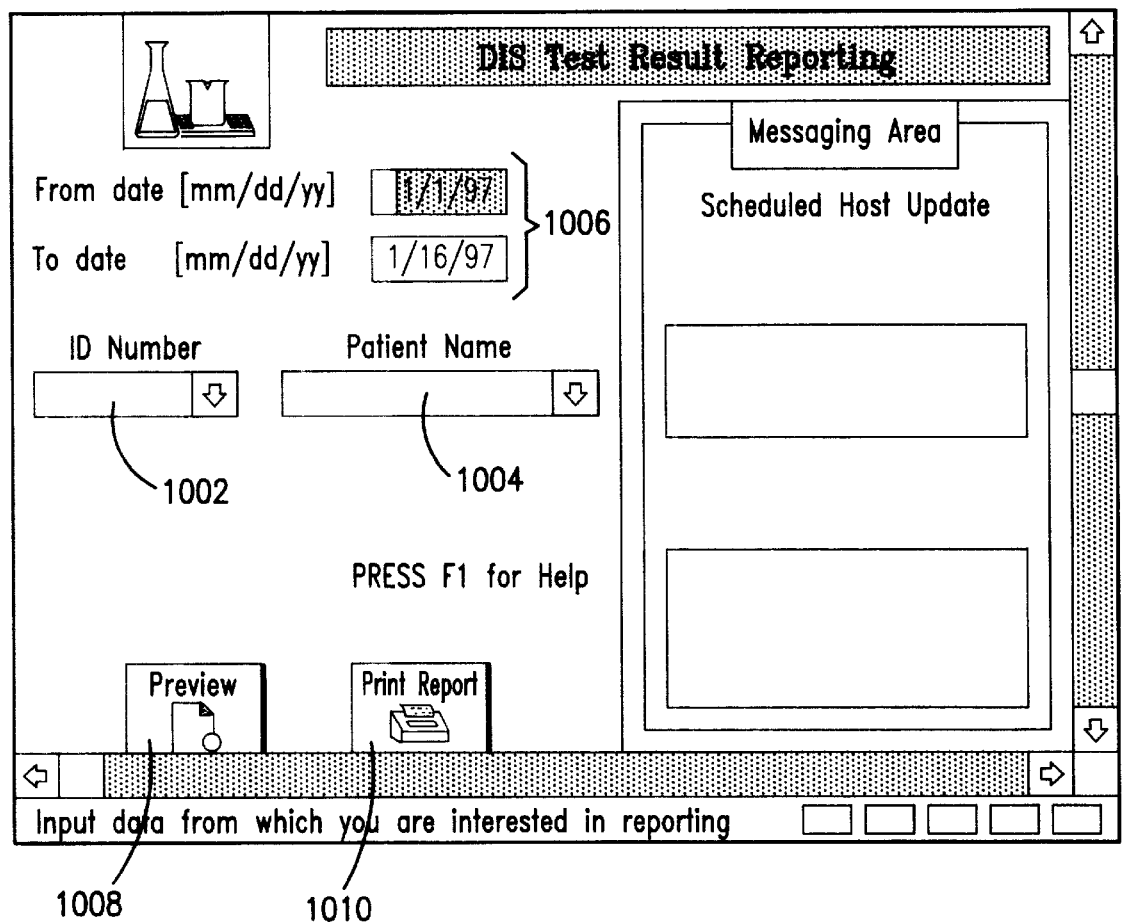
FIG. 10 is a test result reporting input screen.

As noted above, if the user instead chooses to generate a test data report, the client software of FIG. 3 performs a report generation function at block 302. This function permits a hospital computer 202 or a physician computer 206 to review the lab's progress toward completion of scheduled tests as well as to review completed test results. This function is initiated using the test result reporting input screen shown in FIG. 10. The patient's name and a unique ID number assigned to the patient are selected in scroll windows 1004 and 1002 respectively. A range of dates for cumulative results/status reporting can be selected in field 1006. Clicking on button 1008 selects display of the report on screen, and button 1010 prints a hard copy of the selected report.

Figure 11:
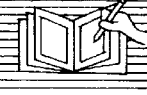
FIG. 11 is a report display selection screen for selecting the portion of the patient record to be displayed.

If button 1008 is selected to display the report on-screen, the selection screen of FIG. 11 is displayed, whereby the physician can select particular categories of test results to be viewed. By clicking on the "buttons" provided in this display screen, the physician can obtain results of tests in the indicated categories. For this purpose, the tests are grouped using the same method used for grouping tests for ordering purposes, as described above. This grouping provides a consistent and clinically sensible interface for the physician when ordering tests and reviewing the results of those tests. By selecting the designated buttons as shown in FIG. 11, the physician also has the option of previewing all reports, printing all reports, returning to the main form, or displaying demographic data for the patient.

After the physician selects display or printing of test results, block 3021 is executed to verify authorization of the requester to review the information contained in a test report. When authorization is requested, a report request packet or packets containing the patient ID, test ID, and date the test was conducted (start and end dates when a report covering a period of time is requested) is transmitted to the patient database computer. When the patient database computer receives report request packets, it verifies that the report request packets originated from either a physician computer 206, or another hospital computer 202. If the message originated from a lab site/subspecialty computer 204 or an insured computer 208, the patient database computer sends a document to the originating computer indicating that the computer is attempting to execute a task it is not authorized to perform and ignores the request. Once the patient database computer verifies that the recipient computer is authorized to receive the test data, the results are transmitted from the patient database computer in a data stream formatted for cumulative results reporting, and displayed for the physician or lab technician with an organization identical to the organization of the tests within the ordering function. This technique indexes and organizes the test results to facilitate analysis and rapid recognition of clinical patterns and trends to facilitate accurate diagnosis.

This format also highlights changes in the results of the same test over time for that patient. Where text information or "notes" are associated with a particular test result, an on-screen indication is provided at the test result, and the notes are accessible on-screen via a hyperlink accessed by clicking on the test result. Test results are displayed on screen with visual aids for identifying values outside a normal range, such as color coding of the text or background and the use of different fonts. Once a physician has reviewed the results of a test and is satisfied that the test was properly conducted, he/she can then update the patient test report screen to indicate that payment for the test is payable.

Figure 12:
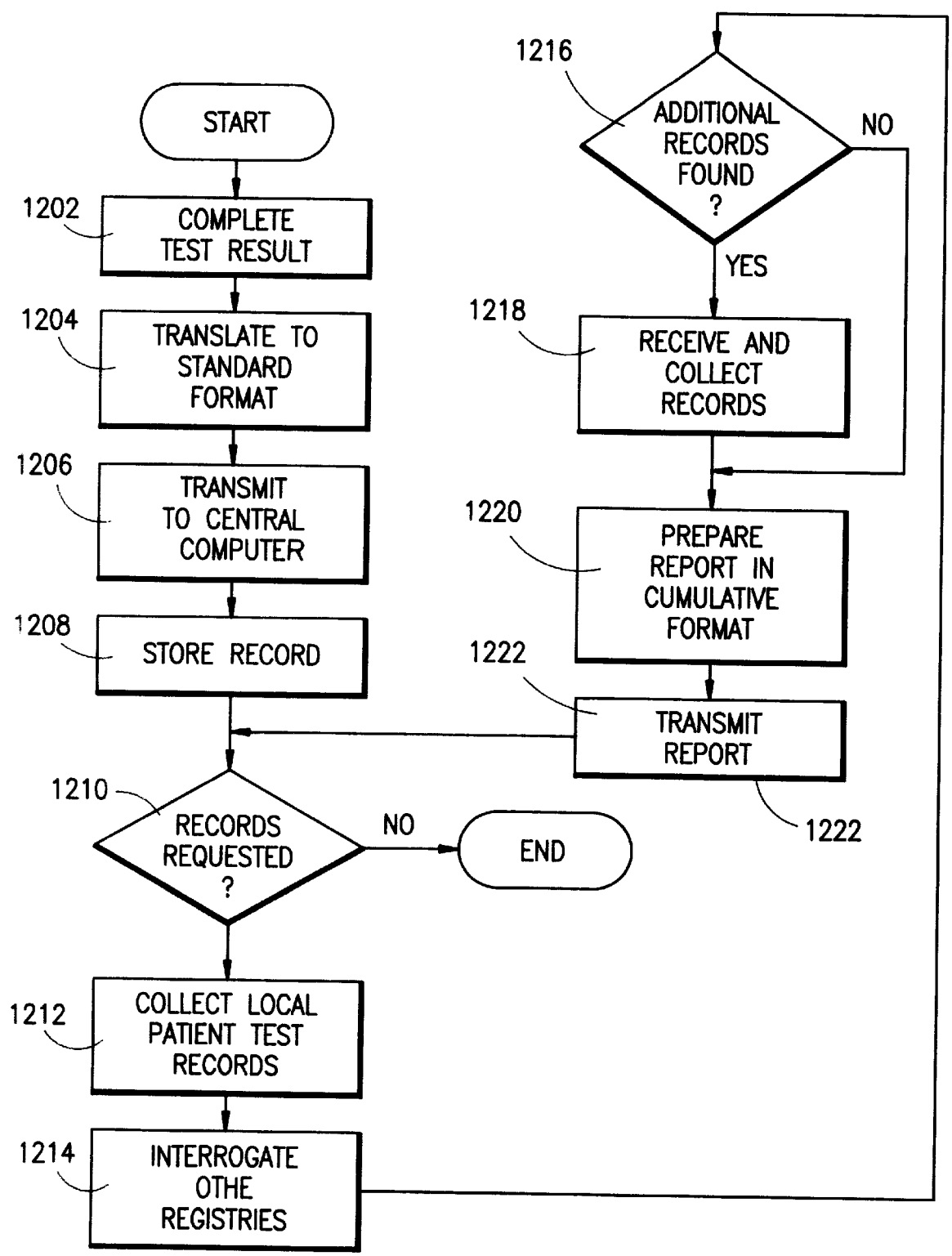
FIG. 12 is a flowchart showing a method of aggregating test results and transmitting them on demand according to the present invention, using a central computer.

FIG. 12 is a flowchart showing a method of aggregating test results and transmitting them on-demand according to the present invention, using a central computer according to the network embodiment of FIG. 2. The functions depicted in FIG. 12 are performed by the server, patient database computer 214 (also shown in FIG. 2). In block 1202, the test results are completed and entered into the system, either directly through automated test equipment interfaced with computer 202 or 204 (shown in FIG. 2), or manually by an operator. In block 1204 the test results are organized in a standardized format, with patient identification, date and time identification, test result values, and any "lab notes" arranged in predetermined fields. The formatted results are then transmitted to central patient database computer 214 in block 1206.

In block 1208, patient database computer 214 receives and stores the test record. The patient database computer may then accept a request for patient test records in block 1210. When the records are requested, control passes to block 1212 and the desired date range of test records for a particular patient are collected and organized in the central computer. Optionally, the central computer may interrogate other repositories connected to the central computer in a communications network, in block 1214. This interrogation will determine whether additional records for that patient are available, for example in a remote locality, as indicated in block 1216. If additional records are found, control passes to block 1218 where the additional records are retrieved from the remote source and added to the overall patient record in the central computer. This optional interrogation of other sources may be wide-ranging, or may be specific based on patient or physician information, or either a general or targeted search request input by the client computer user. In block 1220, all of the available test results conforming to the client request are collected by the server and organized in a cumulative format, whereupon in block 1222, the report is transmitted to the requesting computer. In an alternate embodiment, the server may transmit all of the individual test records in the standardized test record format used for receipt of test results by the server, and the client computer may parse the test records and format the report.

Other layers of data may be attached to the test result output. For example, by clicking on a test, the user may retrieve a clinical description of the test or demographic information. The software provided for the physician's office may include a clinical notes recording feature and a voice control feature.

Figure 13:
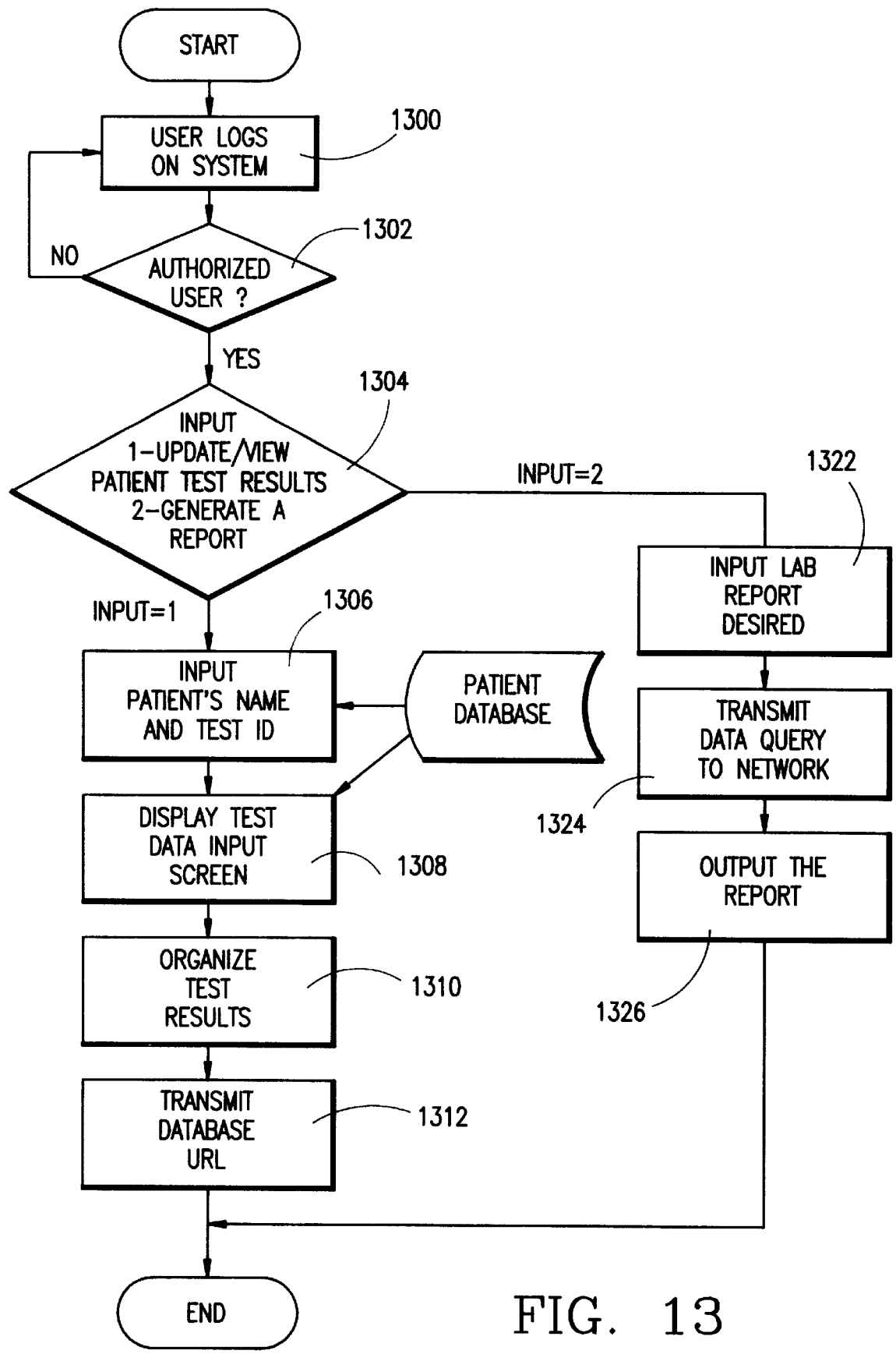
FIG. 13 is a flowchart showing the operation of the test results reporting system and client accounting system.

Referring again to FIG. 2, once a test is ordered, a laboratory technician utilizing a labsite computer 204 is notified of the request to conduct the test. FIG. 13 is a flowchart generally describing the operation of a labsite computer's test results reporting system. Referring now to FIG. 13, the features of the client software include updating/reporting patient test results, and generating test status reports.

Execution of the client program in FIG. 13 begins with block 1300, where the user inputs his/her user name and password to log onto the system. Program control then transfers to block 1302, where the network searches the authorized users list to locate the user's name and password and compare them with the entered values. If the computer does not find a matching combination, it returns execution to block 1300 for the user to try again. After a database number of unsuccessful attempts, the network logs the terminal off the system. If the network determines that the name and password are valid, program control transfers to block 1304, where the program accepts input from the user to either update/view patient test results, or generate a report. This function is preferably performed by displaying an input screen permitting selection of one of the two possible choices.

Referring again to FIG. 13, if a laboratory technician wishes to update/view patient test results, control transfers to block 1306, where the technician is prompted to enter the patient's name and a test ID. Network 211 searches patient database computer 214 for a matching record. If it does not find a match, network 211 sends a message back to the laboratory computer 204 indicating that an existing patient file does not exist and prompts the technician to re-enter the patient name and test ID. After a predetermined number of failures, the network logs off the laboratory computer from the network. When the correct record is found, program control transfers to block 1308, where the network displays the test data input screen into which recorded values for a recently completed test can be entered into the system, either directly through automated test equipment interfaced with computer 202 or 204 (shown in FIG. 2), or manually by an operator. In block 1310 the test results are organized in a standardized format with patient identification, date, and time identification, test result values, and any "lab notes" arranged in predetermined fields. When the laboratory technician has completed the data input, he/she transmits a database update URL containing the patient ID, test ID, test date, logon ID and formatted data to patient database computer 214 in block 1312.

When the patient database computer receives a database update URL, it verifies that the database update URL originated from either a hospital computer 202 or a lab site/subspecialty computer 204. If the message originated from an insured computer 208 or a physician computer 206, the patient database computer sends a document to the originating computer indicating that the computer is attempting to execute a task it is not authorized to perform and ignores the data. Once the patient database computer verifies that the recipient computer is authorized to update the test data, the database of database computer 214 is updated with the new values.

Referring once again to FIG. 13, if a laboratory technician wishes to request a laboratory report of conducted or future tests, program control transfers to block 1322 where the technician is prompted to input the laboratory report desired. This function is preferably performed by displaying an input screen permitting selection of one of the two possible choices. Program control then transfers to block 1324, where the system transmits the information to the network which locates all test data that satisfies the search criteria and then outputs a report in block 1326.

Figure 14:
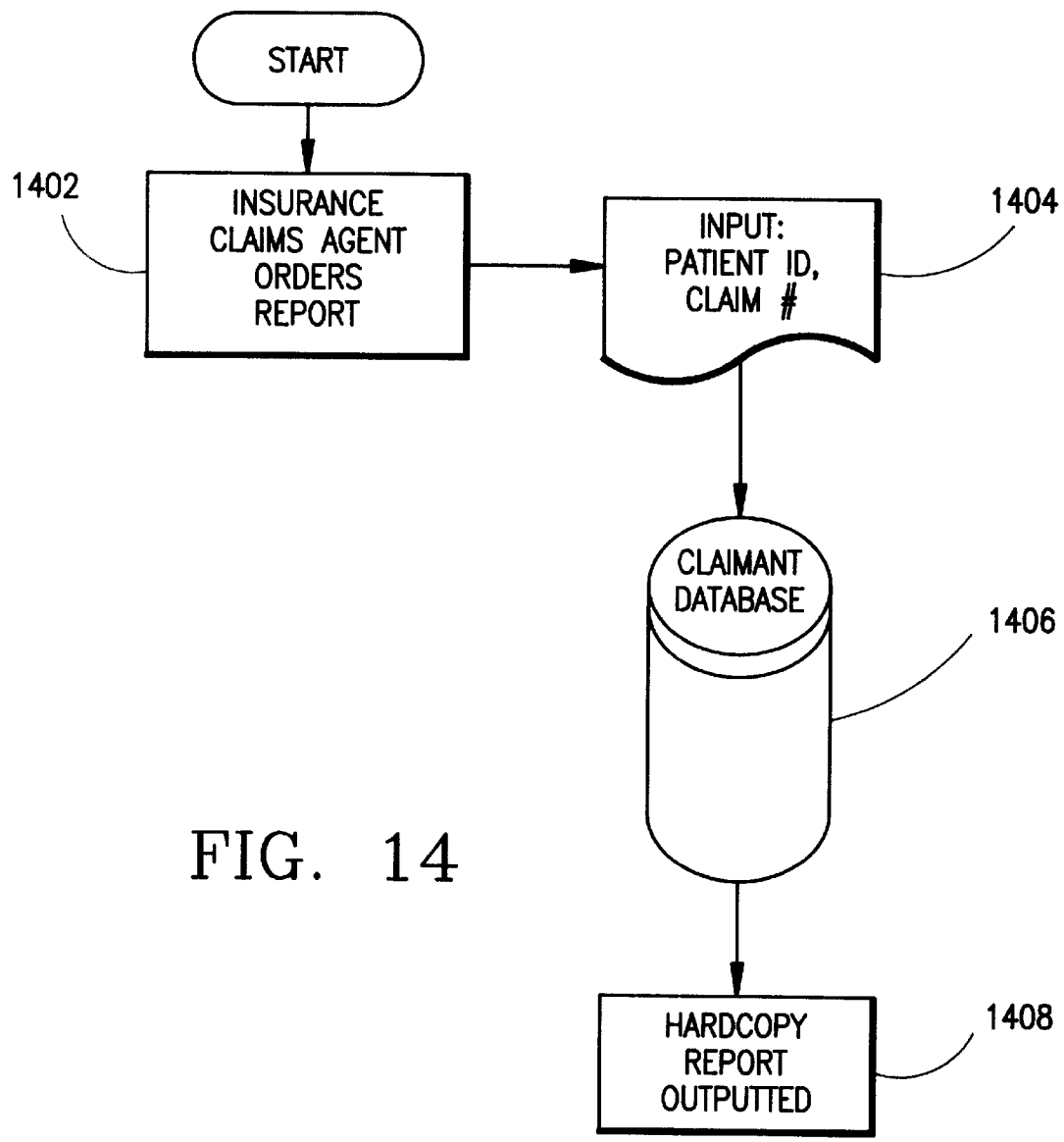
FIG. 14 is a flowchart showing the operation of the report generation function of the insured computer.

FIG. 14 is a flowchart generally describing the operation of an insured computer's report generation function as operable on computer 208 (as seen in FIG. 2). Execution of the client program in FIG. 14 begins much the same way as with the hospital, physician and lab site/subspecialty computers. Once the network determines that the name and password are valid, program control transfers to block 1404, where the program accepts input from the user to generate a report. This function is preferably performed by displaying an input screen permitting input of the desired options. To print a report, an insurance company employee enters the patient ID or claim number. Execution then transfers to block 1406, where the network 211 locates all of the patient records corresponding to the patient ID or claim number and then to block 1408, where the system outputs a hardcopy report.

Figure 15:
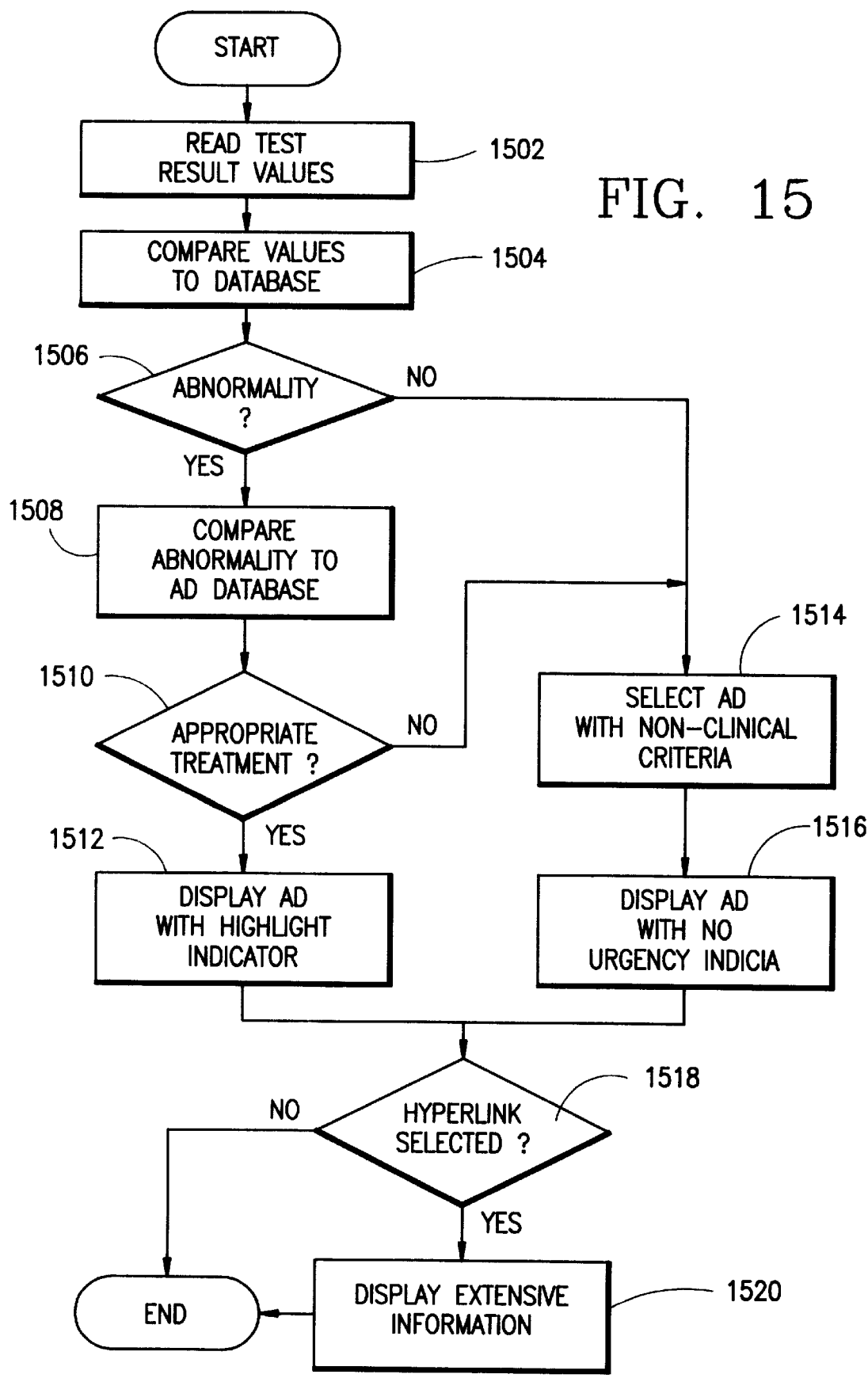
FIG. 15 is a flowchart showing a method of displaying relevant drug treatment advertising according to the present invention.

FIG. 15 is a flowchart showing a novel method of displaying relevant drug treatment advertising according to the present invention.

As shown in FIG. 15, advertising for particular drug treatments may be provided as part of the test results reporting output. In particular, the drug information displayed may be selected based on drugs which are recommended treatments for abnormal clinical results of a particular test. Preferably, the drug treatment advertisement is hyper-linked to full advisory information about the drug, so that the physician can readily obtain information about the possible treatments for conditions suggested by the test results. These advertising features are implemented in software within the client and server computers.

Examining FIG. 15 in detail, the advertising process begins in block 1502 where recent test result values are read by the server computer. These values are compared to information in a database, using an expert system, in block 1504. The expert system determines in block 1506, based on patient demographics, medical history, and the available test results, whether any of the values are abnormal or whether the patient record indicates a potential need for particular medical items. If not, control passes to block 1514 and an advertisement for a drug or other medical device is selected which is not directly related to a condition of the patient diagnosed by the expert system. Alternatively, in this situation, block 1514 may determine that no advertisement is to be displayed. The ad (or no ad) selected in block 1514 is then transmitted to the physician or hospital computers and displayed with the test results.

If an abnormality is found in block 1506, control passes to block 1508. The identified abnormality is compared to an advertising database using the expert system, to determine whether any drugs whose makers have arranged for advertising may be appropriate for treating the abnormality. Offers for other medical equipment, such as local vendor discounts on wheelchairs, oxygen generator rental, etc. may also be displayed. These offers may be displayed based on abnormalities, diagnosis codes, or patient demographic information which suggests a potential need for such medical equipment. For example, a diagnosis of diabetes may suggest patient interest in syringes.

If there is no specific equipment or drug in the database that is determined to be appropriate for the abnormality, control passes to block 1514, and the process proceeds as described above. If an appropriate sponsored drug or item is identified, control passes to block 1516 and the advertisement for that drug or item is transmitted to the physician terminal with the test results, and displayed in a format that highlights the determination by the expert system that the physician may wish to consider this drug as a treatment. This highlighting may be textual, such as display of "Expert System Recommends Consideration:" visual, such as distinctive coloration of the ad or its border, audible, or may use any other highlighting method which will convey to the physician the determination of the expert system that this drug may be worthy of consideration.

It is desirable to provide the physician with a hyperlink from any displayed ad to obtain full manufacturer indications and information about the suggested drug, or more information about equipment offers. After display of any ad, control passes (from both blocks 1516 and 1512) to block 1518. If the hyperlink is selected by the physician, the server provides full information on the medical product described in the ad in block 1520.

Figure 16:
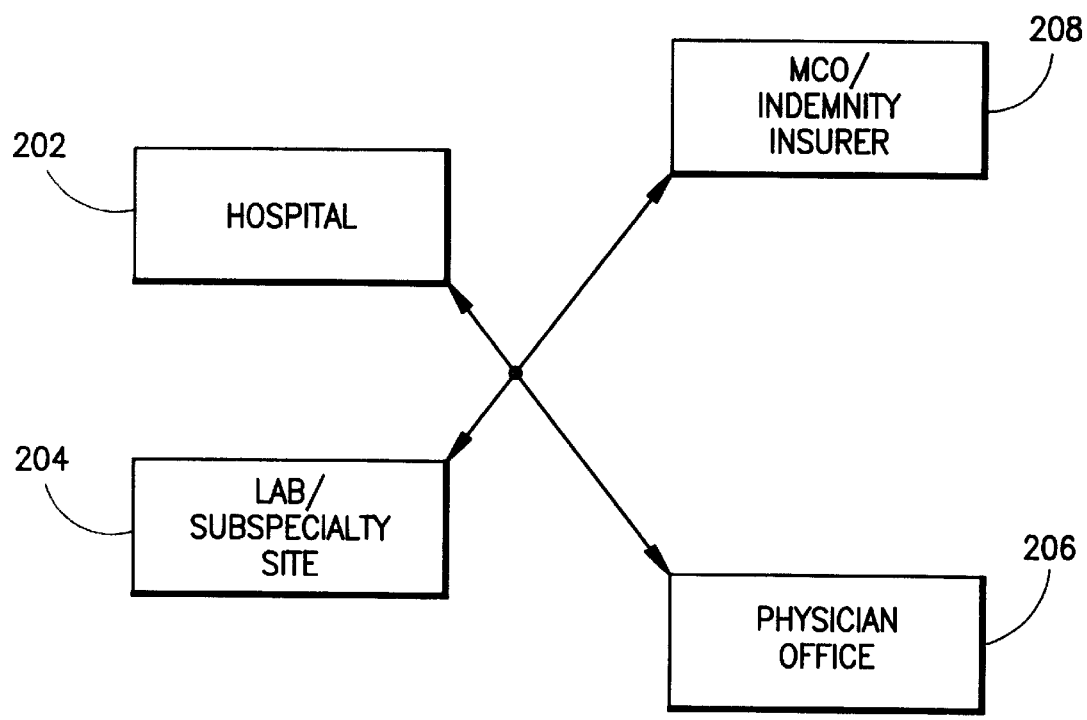
FIG. 16 is a block schematic diagram of an alternative network topology according to the present invention.

FIG. 16 is a block schematic diagram of an alternative network topology according to the present invention. In this alternative configuration, hospital computer 202, physician computer 206, insurer computer 208, and labsite computer 204 are connected in a peer-to-peer network rather than through a central server as in the embodiment of FIG. 2. In general, this embodiment performs the same functions and incorporates the same software features as the server-based embodiment described previously, adapted as appropriate for the differing network topology.

Figure 17A:
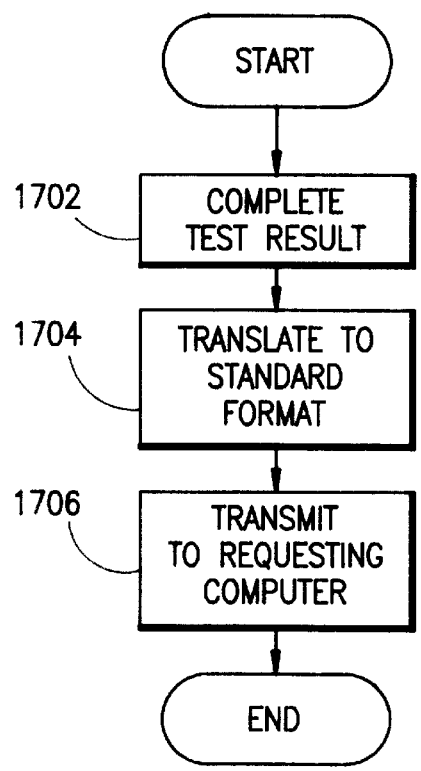
FIGS. 17a and 17b are flowcharts showing an alternative method of aggregating test results according to the present invention using a distributed computing network.
Figure 17B:
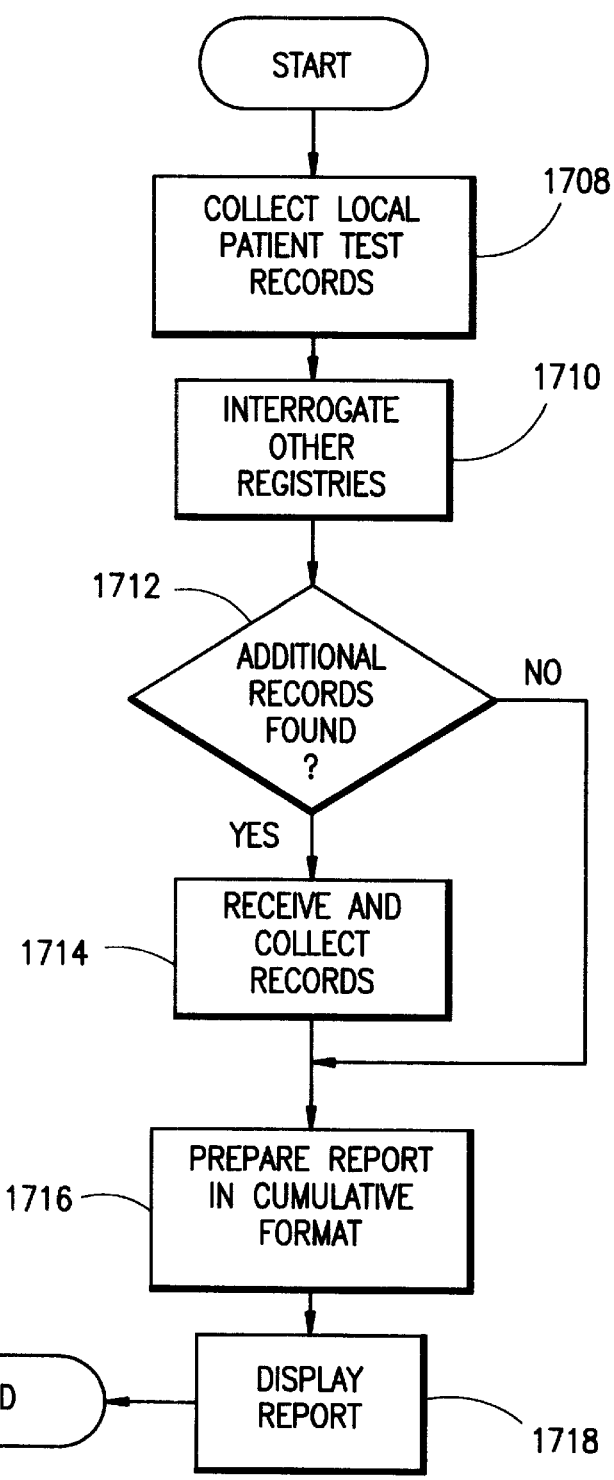

FIGS. 17a and 17b are flowcharts showing an alternative method of aggregating test results according to the present invention using the distributed computing network of FIG. 16.

In this embodiment, the test results are aggregated with previous test results in a patient record, which may be compiled at the physician's office. To compile this record in real time, the physician workstation may perform record merging by connecting to labs, hospitals, HIN record repositories, etc. in sequence to obtain full updated information for the patient. This embodiment of the system avoids the need for a central repository, and facilitates patient record collection by a physician who has not seen the patient previously, for referrals, second opinions, etc. without requiring that records be collected and transferred from another physician's office.

FIG. 17a shows a process for delivering a test result from a hospital or labsite to a receiving computer such as a physician computer 206 or another hospital computer 202. In block 1702, the test results are completed and entered into the system, either directly through automated test equipment interfaced with computer 202 or 204 (as shown in FIG. 16), or manually by an operator. In block 1704 the test results are organized in a standardized format, with patient identification, date and time identification, test result values, and any "lab notes" arranged in predetermined fields. The formatted results are then transmitted to (for example) computer 206 or 208 (shown in FIG. 16) in block 1706.

Referring now to FIG. 17b, the process performed by a computer in the network for displaying a report using the peer-to-peer network of FIG. 16 is shown in detail. In block 1708, the displaying computer (such as computer 206 or 208) receives and stores test records received from a lab and retrieves these and any previously stored records for the selected patient.

In block 1710, the displaying computer interrogates other likely registries and repositories of data using a communications network, such as the internet or a private network, to create a complete cumulative results reporting record for that patient. This interrogation will determine whether additional records for that patient are available, for example in a remote locality. This optional interrogation of other sources may be wide-ranging, or may be specific based on patient or physician information, or either a general or targeted search request input by the client computer user. For example, the sites interrogated may be selectively limited to those hospitals where the patient's physician has privileges and those labs normally used by the physician.

After the records are requested, control passes to block 1712 and, if there are additional records to be aggregated with the records already in the local computer, control passes to block 1714 where the additional records are retrieved from the remote source and added to the overall patient record in the computer. The desired date range of test records for the patient are collected and organized in the computer. In block 1716, all of the available test results conforming to the client request are organized in a cumulative format as described above with reference to U.S. Pat. No. 4,315,309, whereupon in block 1718, the cumulative results report is displayed or printed.

A significant feature of either the central or distributed embodiments of the system is the ability to provide aggregated data and demographic information (with or without patient identification), creating "live" public health statistics through a single query to a central server, or in the case of the distributed system, across multiple hospitals, clinics, labs, and offices. This broad-based information will be useful to HMOs in cost prediction.

When one computer sends a request packet to another computer as described above, this packet may be sent in a standard HTTP (Hypertext Transfer Protocol) or FTP (file transfer protocol) request message. The request message includes components of the URL as described by the standard HTTP or FTP protocol definition. These URL components in the request message allow the server to provide a response appropriate to the URL. The term "URL" as used in the present applications as an example of a "link" which is a pointer to another document or form (including multimedia documents, hypertext documents including other links, or audio/video documents). In this preferred embodiment, documents are transferred to the requesting computer in the form of a success HTTP or FTP response message whereupon the document is packetized and transferred to the requesting computer. When a server sends an account name and password request message to the client, in a preferred embodiment, the account name and password request message is an unauthorized HTTP response. A client computer sends account name and password information to a server as part of an access request message.

Figure 19A:
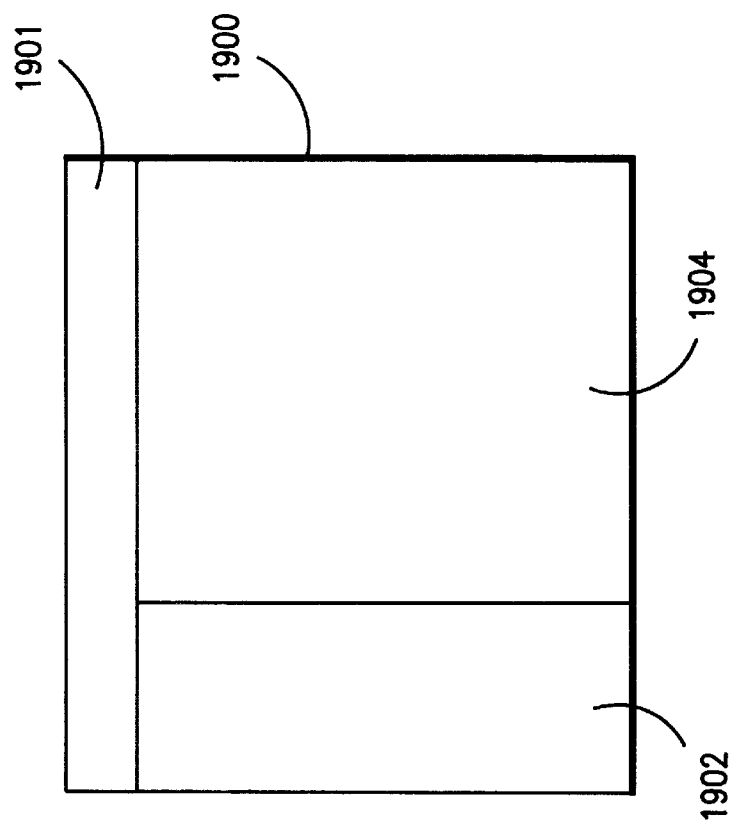
FIG. 19a is a screen display for a web browser frame-based implementation of the user interface of the test ordering and results reporting system.

In this preferred internet-based embodiment, the software operating features and screens described previously may be implemented using a webbrowser interface. FIG. 19a shows a screen display 1900 for a browser based test ordering and results reporting system. This interface may be implemented using Hyper Text Markup Language, for access using the Netscape or Microsoft Internet Explorer browsers. Screen display 1900 includes a browser control panel 1901 at the top of the screen, a control frame 1902, and a display frame 1904. Control frame 1902 contains test results viewing and test ordering selection links organized in the manner described previously for each category of tests. Control frame 1902 preferably includes a "table of contents" with internal links to specific headings for ease of use. For example, control frame 1902 may include, for a particular patient, internal links to microchem tests and subspecialty tests categories. Upon selecting the microchem tests internal link, links corresponding to each one of multiple test subcategories provided for the microchem tests category are provided in control frame 1902 such as, but not limited to, basic hematology, urinalysis, basic chemistry, special chemistry, and microbiology. Further, upon selection of one of these individual subcategory test links within a test category, links corresponding to the individual test or image ordering choices available for the selected subcategory test are provided in control frame 1902 listed either individually or under alphabetical grouping, or in combination thereof. For example, selection of the basic hematology subcategory link within the microchem test category results in HEMOGRAM, DIFF/MORPH, MSCL, or COAG individual test links, as well as links to other individual tests grouped by letter of the alphabet (e.g., "A", "B", etc.), being provided in control frame 1902. Selection of the urinalysis, basic chemistry, special chemistry, or microbiology subcategory links results in a similar display of the individual test links associated with the selected subcategory being provided in control frame 1902. In addition, links associated with a subcategory may include links to images as well as thumbnail pictures of images. Display frame 1904 is used to display the test ordering information and test results obtained by selecting links from control frame 1902. If links for test results are selected, test results in the corresponding category are displayed in display frame 1904. FIG. 20 provides an example of such a test results display for basic hematology test results. Referring now to FIG. 20, test results for a particular patient or test subject are preferably displayed in a spreadsheet format in which results for the individual tests are grouped into columns, and in which each row indicates the particular results for one or more individual tests associated with a particular date and time. Column headings are provided to indicate, without limitation, identification of individual tests for which results are provided (e.g., WBC, RBC, Polys, Bands), one or more displayed test categories (e.g., BASIC HEMATOLOGY), one, or more displayed test subcategories (e.g., HEMOGRAM, DIFF/MORPH), date, and timer For numeric test results, the unit of measurement associated with each test result is indicated. Test results for other categories of tests are displayed in a similar manner. Displayed test results may also include, without limitation, footnotes, lab notes text or notations, images, or other clinical or diagnostic written (or transcribed) comments or observations produced by physicians or technicians.

Figure 19B:
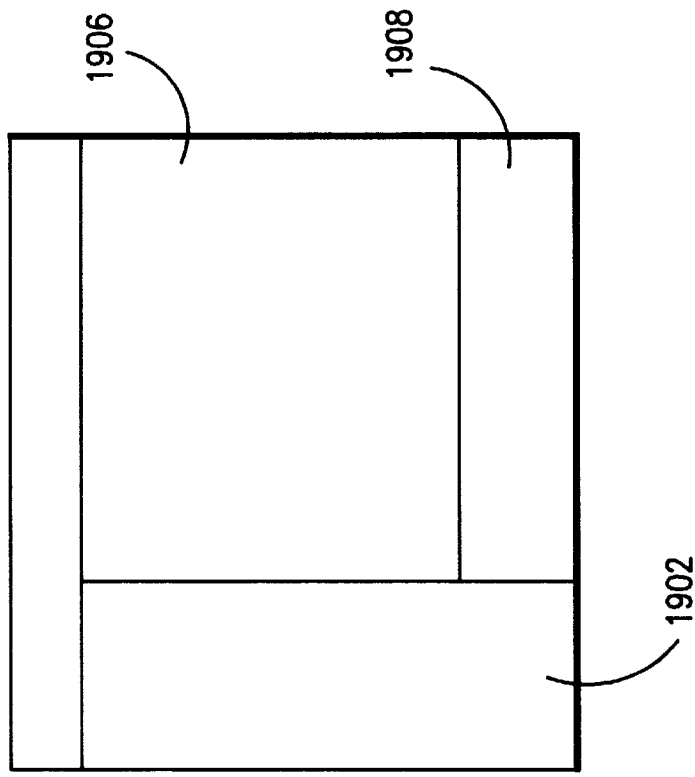
FIG. 19b is a screen display of an ordering screen showing frame arrangement.

If a link for a test ordering function is selected in control frame 1902, a split frame display may be provided as shown in FIG. 19b. Test display frame 1906 displays a list of available tests in the selected category, and may include hyperlinks to addition information about each test. Selection list frame 1908 displays a list of tests which have been selected for ordering. The doctor selects tests from test display frame 1906 by activating a checkbox or hyperlink associated with the desired test, and the selected test is added to the display in selection list frame 1908. Tests may be removed from the selection list in a similar manner. When the test selection is complete and accurate, the doctor may activate a hyperlink to proceed to a further screen (not shown) for laboratory and diagnosis selection.

This browser-based interface provides increased ease of use and implementation compared to proprietary interface methodologies.

Thus, there has been disclosed a novel and improved system and method for on-line ordering of medical tests in a health care network, integrated with an improved system and method for uniformly recording and reporting test results. The system and method are not limited to the specific embodiments disclosed herein, but encompass variations which will be apparent to those skilled in this field upon detailed review of the specification and drawings.

We claim:

1. A network-based test ordering and results reporting system comprising:

medical computing means for computing at a location where medical services are rendered;

test ordering means associated with said medical computing means for displaying a set of available medical laboratory tests in an ordered fashion and permitting designation by an authorized operator of at least one selected test to be performed on an identified patient;

laboratory selection means associated with said medical computing means for retrieving information defining a plurality of laboratories and their testing capabilities, displaying a set of one or more geographically dispersed laboratories capable of performing said selected test, and receiving an identification by said authorized operator of a selected laboratory;

laboratory computing means for computing at said selected laboratory;

data transmission means connected to said medical computing means and said laboratory computing means for transmitting a test order identifying said selected test and patient to said laboratory computing means located at said selected laboratory;

test order processing means associated with the laboratory computing means for receiving said test order, storing said test order, and providing said test order to laboratory personnel; and results reporting means associated with the laboratory computing means for receiving test results from the laboratory, storing said test results, and selectively transmitting said test results to said medical computing means.

2. The system of claim 1 wherein said laboratory selection means further includes participation determining means for retrieving information defining health plan participation for each laboratory, retrieving information defining a health plan associated with the patient, and based on said information, preferentially displaying laboratories participating in a health plan associated with the patient in said displayed set of laboratories.

3. The system of claim 1 wherein said laboratory selection means further includes cost determining means for retrieving information defining test cost for each laboratory, and based on said information, preferentially displaying laboratories having lower cost in said displayed set of laboratories.

4. The system of claim 1 further including insurance carrier computing means, connected to said medical computing means and said laboratory computing means, for receiving a test authorization request from the medical computing means, performing an authorization process, and transmitting an authorization to said laboratory computing means.

5. The system of claim 1 further including central database means, connected to said medical computing means and said laboratory computing means, for receiving and storing test results from at least one said laboratory and transmitting cumulative test results for a patient to said medical computing means.

6. The system of claim 5 wherein said at least one of said medical computing means, said central database means, and said laboratory computing means include software translating means for selectively reformatting incompatible data records.

7. A network-based test ordering and results reporting system comprising:

medical computing means for computing at a location where medical services are rendered;

test ordering means associated with said medical computing means for displaying a set of available medical laboratory tests in an ordered fashion and permitting designation by an authorized operator of at least one selected test to be performed on an identified patient;

laboratory selection means associated with said medical computing means for retrieving information defining a plurality of laboratories and their testing capabilities, displaying a set of one or more geographically dispersed laboratories capable of performing said selected test, and receiving an identification by said authorized operator of a selected laboratory;

laboratory computing means for computing at said selected laboratory;

data transmission means connected to said medical computing means and said laboratory computing means for transmitting a test order identifying said selected test and patient to said laboratory computing means located at said selected laboratory;

test order processing means associated with the laboratory computing means for receiving said test order, storing said test order, and providing said test order to laboratory personnel;

results reporting means associated with the laboratory computing means for receiving test results from the laboratory, storing said test results, and selectively transmitting said test results to said medical computing means;

results display means associated with the medical computing means for displaying the test results;

treatment information storage means connected to the medical computing means for recording treatment information records identifying drugs or medical devices that may be needed by a patient, diagnostic indicia for such drugs or medical devices, and a display element for suggesting consideration of said drugs or medical devices;

display means for accessing said treatment information storage means, and based on displayed test results, displaying said display element associated with a drug or medical device having a diagnostic indicia indicated by said displayed test results.

8. The system of claim 7 wherein said medical computing means further includes means for accessing additional product information via a hypertext link, for a drug or medical device whose associated display element is displayed as relevant to said test results.

* * * * *